US010357395B2

(12) United States Patent
    Miller et al.

(10) Patent No.: US 10,357,395 B2
(45) Date of Patent: Jul. 23, 2019

(54) MENSTRUAL CUP

(71) Applicant: The Flex Company, Venice, CA (US)

(72) Inventors: Andrew Ross Miller, Venice, CA (US);
    Jane Hartman Adamé, Venice, CA (US)

(73) Assignee: The Flex Company, Venice, CA (US)

( * ) Notice: Subject to any disclaimer, the term of this patent is extended or adjusted under 35 U.S.C. 154(b) by 0 days.

(21) Appl. No.: 16/132,122

(22) Filed: Sep. 14, 2018

(65) Prior Publication Data
    US 2019/0083296 A1    Mar. 21, 2019

Related U.S. Application Data

(60) Provisional application No. 62/559,050, filed on Sep. 15, 2017.

(51) Int. Cl.
    A61F 13/15    (2006.01)
    A61F 13/20    (2006.01)
    A61F 5/455    (2006.01)
    A61F 5/44     (2006.01)

(52) U.S. Cl.
    CPC .......... A61F 5/4553 (2013.01); A61F 5/4404 (2013.01)

(58) Field of Classification Search
    CPC ...... A61F 5/4553; A61F 13/2045; A61F 5/44;
            A61F 13/202; A61F 13/2048; A61F
            13/2028; A61F 13/2042; A61F 13/208;
            A61F 5/4407; A61F 6/08; A61B
            5/150045; A61B 2010/0074; A61B
            5/02042
    See application file for complete search history.

(56) References Cited

U.S. PATENT DOCUMENTS

| 1,891,761 A | 12/1932 | Goodard |
| 1,996,242 A | 4/1935 | Hagedorn |
| 2,089,113 A | 8/1937 | Chalmers |
| 2,321,340 A | 6/1943 | Waterbury |
| 3,157,180 A | 11/1964 | Bakunin |
| 3,595,236 A * | 7/1971 | Corrigan ............. A61F 13/2051 604/363 |

(Continued)

FOREIGN PATENT DOCUMENTS

| GB | 2425260 | * 10/2006 | ............. A61F 5/455 |
| WO | 02/080827 | * 10/2002 | ............... A61F 6/08 |

(Continued)

OTHER PUBLICATIONS

International Search Report and Written Opinion for International Application No. PCT/US2018/051187, Search completed Feb. 4, 2019, dated Feb. 25, 2019, 15 Pgs.

Primary Examiner — Michele M Kidwell
(74) Attorney, Agent, or Firm — KPPB LLP

(57) ABSTRACT

A menstrual cup and applicator for use in the vagina. The menstrual cup having a receptacle for holding fluid and having a stem device connected to the top of the cup and extending through the open cavity through the bottom of the cup. The stem is configured to actuate the side and rim of the cup to allow for easier insertion and removal of the cup. The applicator may have several components and is configured to grasp a folded cup and position the cup in a deployed position within the vagina. Additionally, the applicator is designed to aid in the removal of the menstrual cup.

20 Claims, 28 Drawing Sheets

(56) References Cited

U.S. PATENT DOCUMENTS

| | | | |
|---|---|---|---|
| 3,841,333 A * | 10/1974 | Zalucki | A61F 5/4553 604/330 |
| 4,486,191 A * | 12/1984 | Jacob | A61F 13/2051 604/330 |
| 4,799,929 A | 1/1989 | Knowles | |
| 4,810,247 A * | 3/1989 | Glassman | A61F 5/453 604/171 |
| D323,212 S | 1/1992 | Crawford | |
| 5,342,331 A | 8/1994 | Silber et al. | |
| 5,476,455 A * | 12/1995 | Silber | A61F 5/4553 604/330 |
| 5,827,248 A * | 10/1998 | Crawford | A61F 5/4553 604/328 |
| 6,168,609 B1 * | 1/2001 | Kamen | A61F 5/4553 600/573 |
| 6,264,638 B1 | 7/2001 | Contente | |
| 8,795,248 B2 * | 8/2014 | Shihata | A61F 5/4553 604/327 |
| 10,016,308 B2 * | 7/2018 | Knox | A61F 15/005 |
| 2008/0077097 A1 * | 3/2008 | Chambers | A61F 5/4553 604/330 |
| 2011/0094519 A1 | 4/2011 | Gopal et al. | |
| 2013/0138135 A1 * | 5/2013 | Rosen | A61B 17/12 606/197 |
| 2015/0164680 A1 * | 6/2015 | Chen | A61F 5/4553 604/330 |
| 2015/0202076 A1 | 7/2015 | Wijzen | |
| 2017/0189222 A1 * | 7/2017 | Lin | A61F 5/4553 |
| 2018/0028350 A1 * | 2/2018 | Wilson | A61F 5/4553 |

FOREIGN PATENT DOCUMENTS

| | | | | |
|---|---|---|---|---|
| WO | 2007/082341 | * | 7/2007 | A61F 5/455 |
| WO | 2015/012776 | * | 1/2015 | A61F 5/455 |

* cited by examiner

MENSTRUAL CUP

CROSS-REFERENCED APPLICATIONS

This application claims priority to U.S. Provisional Patent Application No. 62/559,050 filed on 15 Sep. 2017. The enclosure of which is included herein by reference in its entirety.

FIELD OF THE INVENTION

The present invention generally relates to menstrual cups and methods of their use.

BACKGROUND OF THE INVENTION

Menstrual cups have been in use and have been known as is described further in U.S. Pat. No. 1,891,761 to Goddard, U.S. Pat. No. 1,996,242 to Hagedom, U.S. Pat. No. 2,089,113 to Chalmers, U.S. Pat. No. 5,827,248 to Crawford, and Design Pat. No. D323,212 to Crawford. Such devices are commonly used as a replacement to other catamenial devices such as tampons and sanitary napkins.

The typical menstrual cup is a cup like device designed to be inserted into the vagina and catch the menses. Traditional menstrual cups form a seal with the vaginal wall that must be disrupted before the cup is removed. Air equalization holes present on traditional cups equalize air pressure above and below the cup when a user depresses the sidewall rotating the equalization holes into a vertical orientation. Traditional menstrual cups are designed for multiple reuses and can be inserted and removed at the will of the user.

However, known menstrual cups have many disadvantages. The ease of insertion and removal can present certain difficulties that may lead users to resort to less ideal methods of collection. For example, known cups generally lack a function to aid in the removal of the cup, having only a small gripped stem which when pulled and due to the seal formed between the cup and the vagina creates a mechanical suction force between the cup and the vagina and cervix prohibiting, not aiding, removal. Cups are also difficult to insert. Existing cups are inserted with specific fold techniques that require dexterity and grip strength to maintain the folded shape and requires the user to insert their fingers into the vagina. It is difficult to perform insertion with existing cups, particularly for individuals with loss of dexterity or grip strength. Further, for proper functioning without leakage, the cup must be completely unfolded within the vagina, however, existing menstrual cups often do not completely unfold under their own mechanical spring forces and require a user to reach further into the cavity to inspect the shape and if necessary manipulate the cup to complete the unfolding. If existing cups are not placed ideally within the body, the wearer may experience leakage and discomfort.

Therefore, there is a need for an improved menstrual cup which overcomes one or more of the disadvantages of the prior art.

BRIEF SUMMARY OF THE INVENTION

The application is directed to menstrual cups that improve on the use and function over the prior art, and methods of their use.

Some embodiments are directed to a menstrual cup that has a receptacle with a resiliently foldable rim defining a generally circular perimeter in an unfolded state. Additionally the cup has a sidewall with an inner wall surface that defines a cavity therein. Furthermore, the cavity has a top portion proximal to the foldable rim with a first opening and a bottom portion with a second opening, wherein the cavity is configured to collect a fluid. Additionally, the cup is configured with an elongated stem having a proximal end and a distal end and an elongated middle portion therebetween. The stem seats within the second opening to form a fluid seal. The elongated stem is configured to apply a pulling force to the inner wall surface when a pulling force is applied to the distal end thereof. The receptacle may be configured into two separate positions. A folded position exists where a portion of the foldable rim is deformed to extend at least a portion of the top portion inward towards the center of the cavity. A deployed position also exists where the foldable rim is unfolded such that the first opening of the top portion conforms to the generally circular perimeter of the unfolded resiliently foldable rim.

In other embodiments, the bottom portion of the cup is further configured to form an interference fit with the stem.

In still other embodiments, the stem further comprises a stop disposed at a point along the length of the stem.

In yet other embodiments, the cup is formed of a material selected from a group consisting of silicone material and a thermoplastic elastomer.

in still yet other embodiments, the seal is configured to be reinforced material such that it is thicker than the sidewall.

In other embodiments, the seal is selected from a group consisting of a radial seal and a wiper seal.

In still other embodiments, the stem comprises a resiliently foldable ring configured to cooperatively engage with a groove formed into the foldable rim and the side wall of the receptacle such that the depth of groove does not exceed the thickness of the sidewall, and wherein the ring is configured to pull against the foldable rim, sidewall, and inner wall when the stem is actuated and pulled by the user.

In yet other embodiments, the stem is a continuous extension of the foldable rim.

In still yet other embodiments, the stem further comprises an elongated aperture configured to extend from the proximal end through the distal end whereby air pressure may be appropriately balanced in each of the folded and deployed positions.

In other embodiments, the cup comprises at least one hole to equalize the pressure for the removal of the cup.

In still other embodiments, the at least one hole is disposed through the elongated stem.

In yet other embodiments, the at least one hole is disposed through the sidewall of the cup near the top portion.

In still yet other embodiments, the distal portion of the stem further comprises grip enhancements.

In other embodiments, the grip enhancements are selected from a group consisting of ridges, spiral ridges, a loop, a ring, and independent structures.

In still other embodiments, the cup is coated in parylene.

In yet other embodiments, the proximal end of the elongated stem is connected to the inner wall of the receptacle and the elongated middle portion is configured to pass through the cavity and the second opening of the bottom portion of the receptacle such that the distal end extends below the receptacle.

In still yet other embodiments, the ring is overmolded into the cup.

In other embodiments, the stem is a string wherein the string is molded into the cup.

In still other embodiments, the string is molded into the cup by a method selected from a group consisting of co-molding and overmolding.

Other embodiments include an applicator tool for a menstrual cup that has a cylindrical body with an outer wall and a contoured inner wall defining a conical cavity near a top portion thereof. Additionally, the applicator has at least two elongated paddles slidingly engaged with the cylindrical body which have a proximal end and a distal end wherein the elongated paddles are connected near the proximal end and separated at the distal end such that the proximal end of the paddles is configured to engage with the body of a menstrual cup. Furthermore, the actuator has an actuator mechanism with a distal end and a proximal end and is configured to slidingly engage with the cylindrical body whereby the opening of the distal end engages with a menstrual cup stem and interferingly closes on the stem when slid proximally through the cylindrical body. The actuator mechanism has an insertion and removal position such that the interfering engagement with the menstrual cup causes a folding of the cup by way of an axial displacement of the mechanism distal from the cup. The actuator mechanism has a deployed position wherein the actuator mechanism may release the engagement with the cup and the at least two paddles may be configured to concentrically cradle the cup as the paddles are slid in an upward motion to insert the cup.

In other embodiments, the cylindrical body further comprises a plurality of ridges disposed on the inner wall thereof and are configured to define a constriction area near the top portion of the applicator such that the engagement with the paddles and the applicator results in a contact with a menstrual cup.

In still other embodiments, the actuator mechanism is a splayed plastic stem that passes through the constriction area where the maximum distal position relates to a maximum radial opening and the maximum proximal position relates to a minimum radial opening.

Other embodiments may include a method of inserting a menstrual cup that requires obtaining a menstrual cup. Then obtaining an applicator, that has a cylindrical body having an outer wall and a contoured inner wall defining a conical cavity near a top portion thereof. Additionally, the applicator has at least two elongated paddles slidingly engaged with the cylindrical body and having a proximal end and a distal end wherein the elongated paddles are connected near the proximal end and separated at the distal end and wherein the proximal end of the paddles is configured to engage with the body of a menstrual cup. The applicator has an actuator mechanism having a distal end and a proximal end and configured to slidingly engage with the cylindrical body and the at least two paddles such that the actuator mechanism is concentrically disposed between the elongated paddles and interferingly engage with a menstrual cup near the top portion of the cylindrical body. The actuator mechanism has an insertion and removal position such that the interfering engagement with the menstrual cup causes a folding of the cup by way of an axial displacement of the mechanism distal from the cup. Additionally, the actuator mechanism has a deployed position wherein the actuator mechanism may release the engagement with the cup and the at least two paddles may be configured to concentrically cradle the cup as the paddles are slid in an upward motion to insert the cup. Then the menstrual cup may be folded into the described applicator and subsequently deployed. by way of the applicator.

Other methods include a method of manufacture of a menstrual cup that includes designing an inverted menstrual cup has a receptacle with a resiliently foldable rim defining a generally circular perimeter in an unfolded state. Additionally the cup has a sidewall with an inner wall surface that defines a cavity therein. Furthermore, the cavity has a top portion proximal to the foldable rim with a first opening and a bottom portion with a second opening, wherein the cavity is configured to collect a fluid. Additionally, the cup is configured with an elongated stem having a proximal end and a distal end and an elongated middle portion therebetween. The stem seats within the second opening to form a fluid seal. The elongated stem is configured to apply a pulling force to the inner wall surface when a pulling force is applied to the distal end thereof. The receptacle may be configured into two separate positions. A folded position exists where a portion of the foldable rim is deformed to extend at least a portion of the top portion inward towards the center of the cavity. A deployed position also exists where the foldable rim is unfolded such that the first opening of the top portion conforms to the generally circular perimeter of the unfolded resiliently foldable rim.

Additionally mold tooling configured to align with the inverted design of the menstrual cup must be obtained.

Once tooling and design are complete, the cup may be molded using the tooling. and then the cup may be extracted from the tooling. Finally, the cup must be reverted to the desired final shape.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION OF THE INVENTION

Turning now to the drawings, many embodiments include a menstrual cup and an applicator system for improved insertion and removal of a menstrual cup in the vagina, along with their methods of use.

In many embodiments the menstrual cup includes a body defining a receptacle extending from an open top portion to bottom portion, the bottom portion being configured with an opening, and a stem that connects to the sidewall of the cup (e.g. along the length or near the top portion) and extends through the interior receptacle area through the opening in the bottom portion, such that the stem is accessible from below the cup. In many embodiments, the stem may mechanically actuate the sidewall of the cup where it connects such that the actuation of the stem also actuates the sidewall of the cup creating a fold along the sidewall of the cup disrupting the seal with the vagina and allowing for removal.

Figure 1:
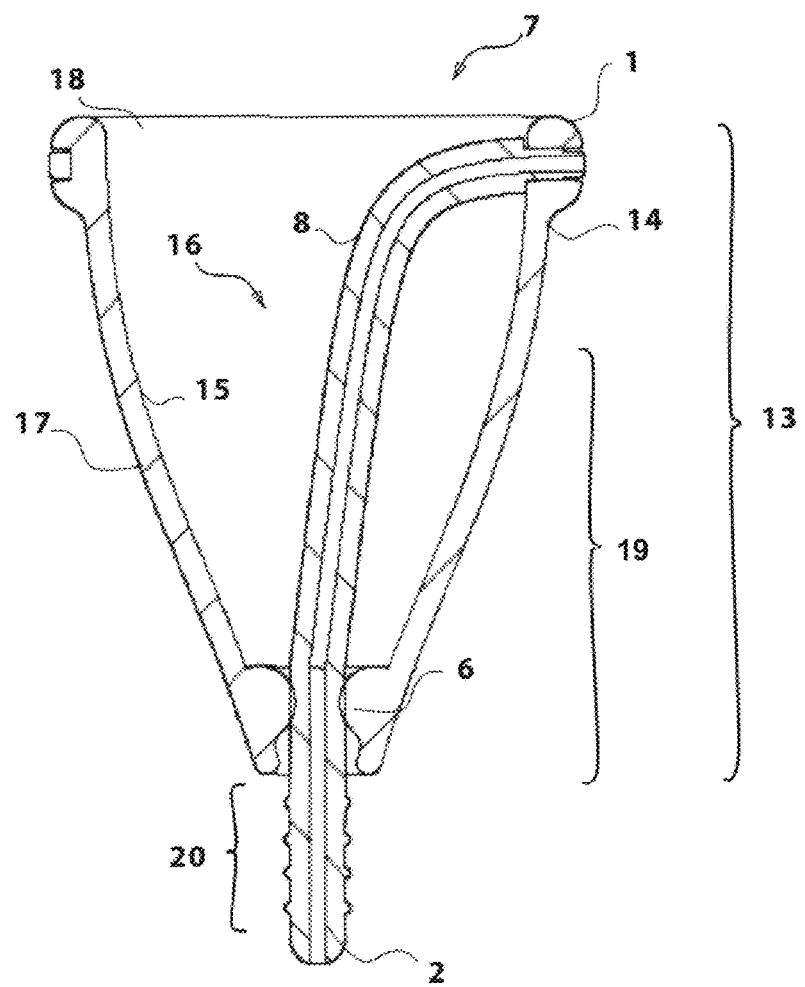
FIG. 1. illustrates a cross sectional view of an embodiment of the invention.

In many embodiments the receptacle includes a wall having an inner wall surface defining a cavity adapted for collecting fluid and an opposed outer wall surface. The open top has a predetermined diameter corresponding to an anatomical fit within the vagina, and a lip with predetermined thickness and rigidity that is adapted to be flexible and resilient. The opening in the bottom portion of the cup may comprise a seal that interfaces with the stem component to prevent any leakage from the receptacle. The stem may further extend below the opening in the bottom portion so that it can be gripped and used for removal of the cup. When pulled from the bottom of the cup, the stem deforms the sidewall (e.g., near the top opening) into a predetermined shape to aid in the removal of the cup from the vagina with minimal leakage and to aid in the pouring out of menses after the cup is removed General Assembly As illustrated in FIG. 1, a menstrual cup in accordance with many embodiments of the invention is indicated generally by the numeral 7. The cup and stem assembly, 7, which is adapted for use in a vagina (not shown), in accordance with many embodiments, includes a receptacle portion 13 which is made up of a sidewall 14 forming a conical like shape. The sidewall 14 may comprise an inner wall surface 15 which defines a cavity 16 adapted for collecting fluid (not shown) and an outer wall surface 17. The receptacle 13, in accordance with many embodiments, may be somewhat elongated and generally extends from an open top or upper portion 18 to an opening located in a bottom or lower portion 19 wherein the bottom/lower portion 19 may be smaller in diameter than the top end 18. In some embodiments the cup 7 may form a conical shape. According to many embodiments, the lower portion 19 may be configured with a seal 6, as will be further described herein. In accordance with many embodiments, the cup assembly 7 may also include a stem 8 which may be attached to an inner wall surface 15 along the length of the sidewall 14. In various embodiments the attachment point may be near the top of the sidewall, e.g., just below the rim 1. In numerous embodiments, the stem 8 extends through the cavity 16 and past the seal 6 and comprises a gripped bottom end 20 that can be grasped below the cup.

The cup assembly 7, according to many embodiments, may have at least two configurations; a deployed configuration and a folded configuration. FIG. 1 generally illustrates the cup 7 in a deployed configuration where the rim 1 and sidewall 14 define generally a circular perimeter in an unfolded state. In many embodiments, the cup 7 generally is made of a resilient material allowing it to be foldable into the folded configuration. The deployed configuration allows the rim 1 to form a seal between the cup 7 and the vaginal walls (not shown). The folded configuration will be explained in greater detail in reference to other figures.

Embodiments of the Stem

Figure 2:
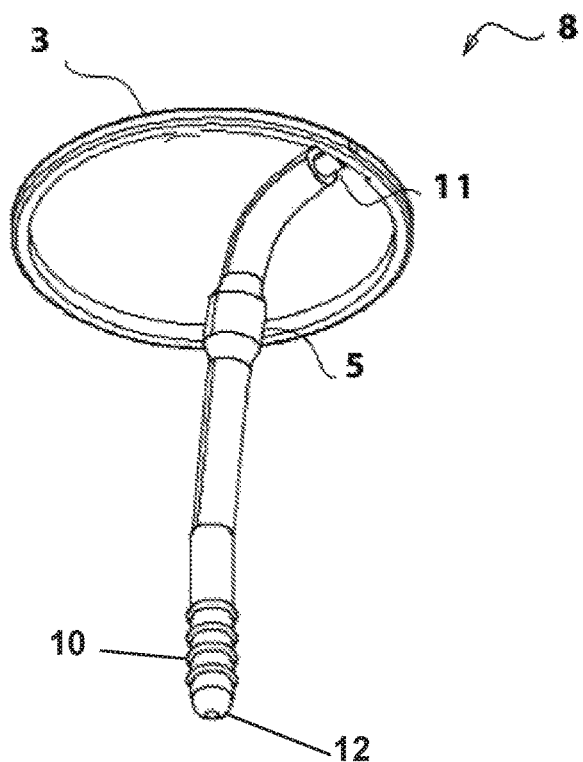
FIG. 2 illustrates an embodiment of the stem for use in the menstrual cup.

As previously discussed many embodiments include a stem 8 that is attached in some fashion to the sidewall of the cup near the upper portion thereof. FIG. 2, in accordance with some embodiments illustrates an embodiment of the stem 8. Some embodiments may include the stem 8 as being a separate portion of the menstrual cup that can be removed. As illustrated in FIG. 2, the stem 8 may comprise an elongated portion having a proximal end 11 and a distal end 12 wherein the distal end is configured to be inserted through the bottom portion 19 of the menstrual cup; more specifically through the seal 6 as illustrated in FIG. 1.

Illustrated in FIG. 1 but described as an embodiment of the stem 8, many embodiments may include an aperture 2 disposed within the stem 8. The aperture, according to some embodiments, when disposed within the stem 8, may run the entire length of the elongated portion of the stem 8 from the proximal end 11 to the distal end 12. Such aperture is designed to equalize air pressure inside and outside the cavity during removal and insertion of the menstrual cup 7. The aperture 2 is closed off by the vaginal walls (not shown) when the cup is in a deployed shape (shown in FIG. 1) allowing for a suction seal to be formed when in use. For removal, pulling the stem 8 from below orients the aperture 2 vertically thereby creating a conduit for air between the region above and below the cup. Thus, pulling the stem 8 configured with the aperture aids in breaking the seal to facilitate the removal of the cup. The cup configured with an aperture allows the user to remove the cup without the need to compress the sidewall 14 of the cup with their fingers to break the seal FIG. 2 further illustrates a stem with a ring portion 3 that is connected to the elongated stem portion at the proximal end 11, according to various embodiments described herein. In such embodiments, the ring portion may be configured to attach to the sidewall 14 of the menstrual cup 7 as will be described in more detail with respect to the cup portion. The ring portion 3, according to many embodiments, may be manufactured of a similar material as the cup 7 and the stem 8 such that it will allow for resilient manipulation during the actuation process described throughout this specification. The connection of the proximal end 11 to the ring, according to many embodiments, may function as an interference fit such that the connection is secure and will not disconnect during actuation. When the stem is actuated the resilient ring portion 3 may resiliently deform in coordination with the sidewall 14 of the cup 7 such that the sidewall 14 of the cup is actuated and creates the fold previously mentioned.

During use, as the menstrual cup 7 is actuated according to embodiments describe herein, the stem 8 may move through the open bottom end 19 of the menstrual cup 7. With such movement, the stem may be configured to prevent over deformation of the cup 7 such that any retained liquid may escape the receptacle 13 of the cup 7. Many such embodiments of the stem have a stop portion 5 disposed along a portion of the length of the stem. The stop may be made of similar material and may also be an integral portion of the stem 8. The stop 5, according to many embodiments, encompasses the diameter of the stem and has a larger diameter than the stem itself. The larger diameter prevents the stem 8 from being pulled too far through the seal 6 of the cup 7 and only allowing the sidewall 14 to deform a predetermined distance and provides that additional force applied to the stem 7 after the stop 5 is bottomed out on the cup 7 is transmitted to the cup 7 aiding in removal.

Many embodiments of the stem 8 may be configured with a grip portion by which the stem may be easily grasped by the user. For example, FIG. 2 illustrates a stem according to some embodiments that may incorporate dimensional ridges 10 radially displaced along the length of the stem near the distal end 12. Such ridges 10 may allow for a user to better grasp the stem to aid in removal of the cup 7.

Figure 3:
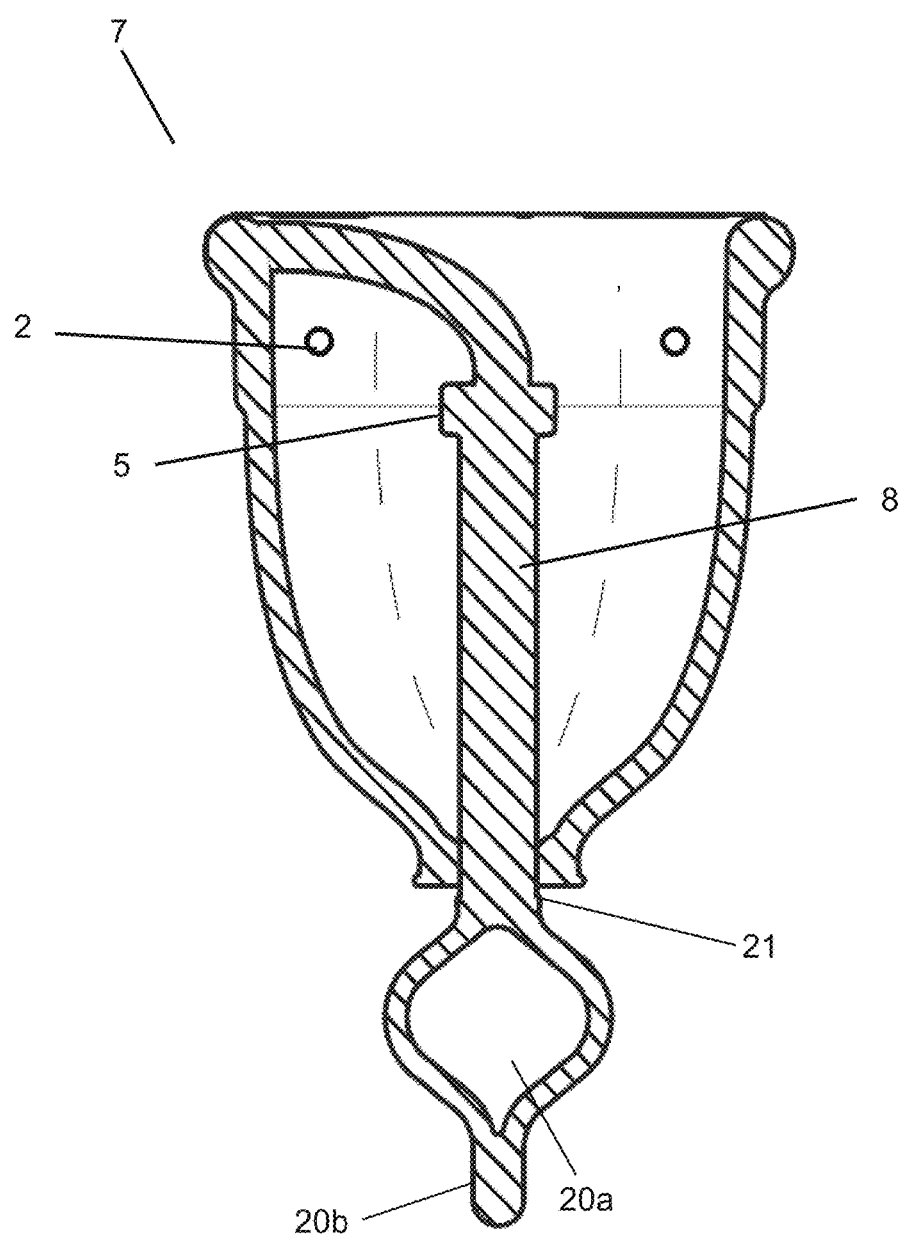
FIG. 3 illustrated an exemplary embodiment of the stem as part of the menstrual cup.

In accordance with other embodiments, FIG. 3 illustrates a stem 8 in which the distal end 12 of the stem 8 may comprise an opening 20A. The opening 20A may be configured to allow a user to grip the stem 8 with a single digit as may be further illustrated in FIG. 9B. Embodiments with the opening 20A are configured to facilitate the actuation of the sidewall 14 by users with decreased dexterity that may not be able to adequately grasp the stem 8 with a pinch grip. The opening 20A, according to many embodiments, may be configured in the shape of a loop or ring. Furthermore, in accordance to many embodiments the stem 8 configured with the opening 20A may also have a small portion 20B thereof extending below the opening 20A to provide an additional means for grasping the stem 8 and actuating the cup 7. In accordance with many embodiments, the opening 20A may be a continuous part of the stem 8, in other words it may be formed as a part of the stem rather than added later. In accordance with many embodiments, the stem 8 configured may also have a small ridge 21 that may provide users with tactile feedback indicating the nominal stem position when a user resets the stem 8 by pulling on the stem 8 from above the top opening 18.

Furthermore, FIG. 3 illustrates a stem 8 continuously incorporated into the rim 1 and sidewall 14 of the cup 7 as may be incorporated into many embodiments. The continuous incorporation of the stem 8 into the rim 1 and sidewall 14 of the cup 7 can improve manufacturability and reduce the number of parts to be cleaned after use.

Figure 4:
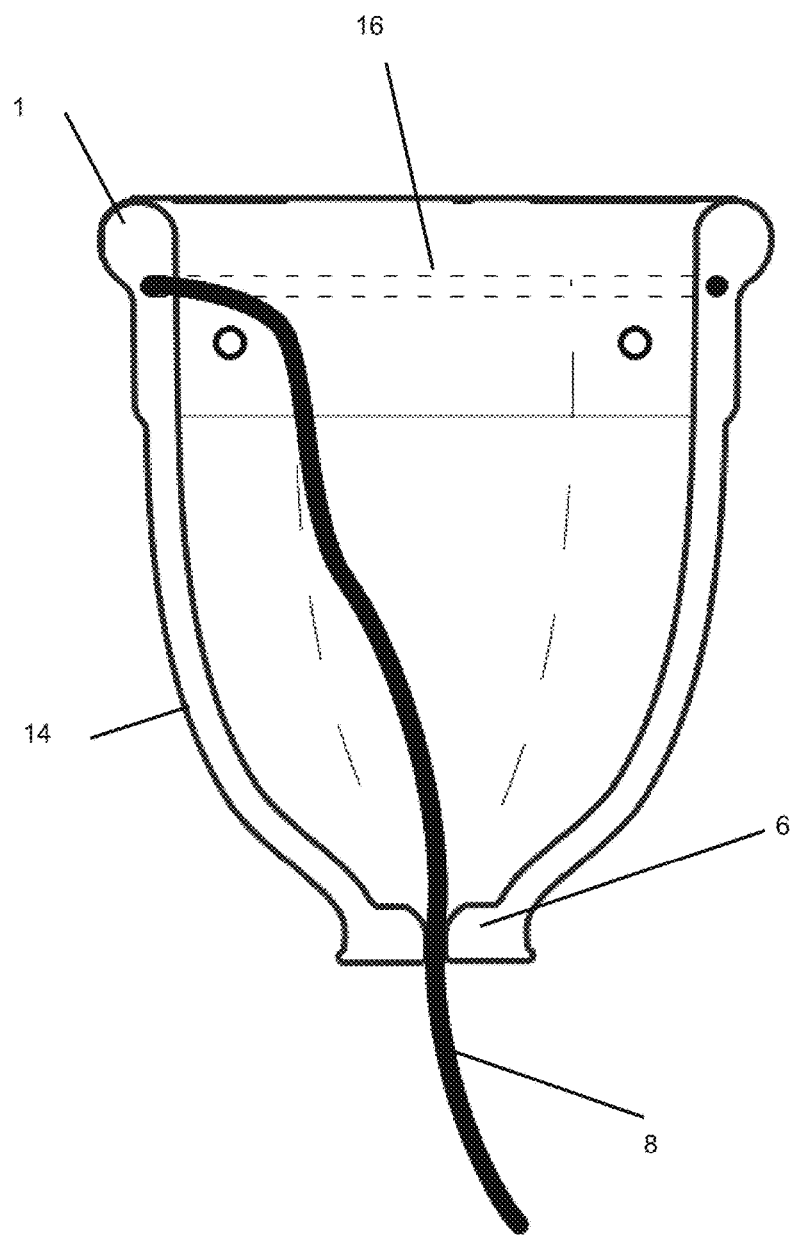
FIG. 4 illustrates an embodiment of the stem of the menstrual cup.

Other embodiments of the stem, as illustrated in FIG. 4 may include a simple string mechanism 8a. The string mechanism may be disposed in a similar manner as any other embodiment of the stem 8, wherein the proximal portion is connected to the rim 1 in the upper portion 18 of the cup and the distal portion extends through the sidewall 14 in the lower portion 19 of the cup. Although certain embodiments are illustrated, it should be understood that the stem 8 may take on any number of forms that are suitable to better facilitate the removal of the cup 7.

Embodiment of the Cup

Figure 5:
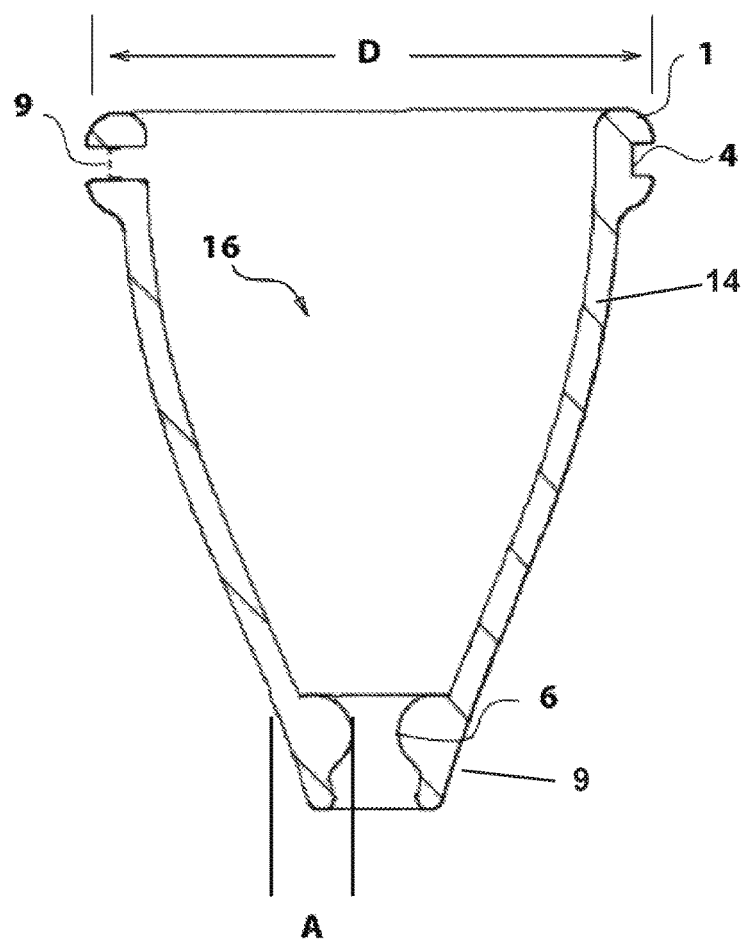
FIG. 5 illustrates an embodiment of the menstrual cup.

Turning now to FIG. 4 as previously discussed the menstrual cup has a receptacle portion that forms an inner cavity 16 for collecting fluid (not shown). In accordance with many embodiments the cup 7 may comprise a seal 6 located near the bottom portion 19 of the receptacle. According to many embodiments, the seal 6 is annular in shape with an interference fit that engages with the portion of the stem 8 passing therethrough to thereby creating a fluid impenetrable barrier (fluid not shown) and allowing the cavity 16 to collect fluid (not shown). In accordance with many embodiments the seal preferably has a reinforced sidewall with a thickness that is greater than that of the sidewall 14 of the receptacle 13. This increased thickness is illustrated as dimension A in FIG. 5.

In other embodiments, the receptacle may be configured with a groove 4 that runs radially and is located near the rim 1 of the cup. The groove may be configured to cooperate with a ring attached to the stem 8, discussed in reference to FIG. 2. Additionally, embodiments of the cup 7 that incorporate the stem 8 with a ring 3 may have a connection hole 9 disposed through the rim 1 of the cup and configured to allow the proximal end 11 of the stem 8 to engage with the ring 3 of the stem thus creating an interconnected stem 8 and cup 7 assembly.

Figure 6:
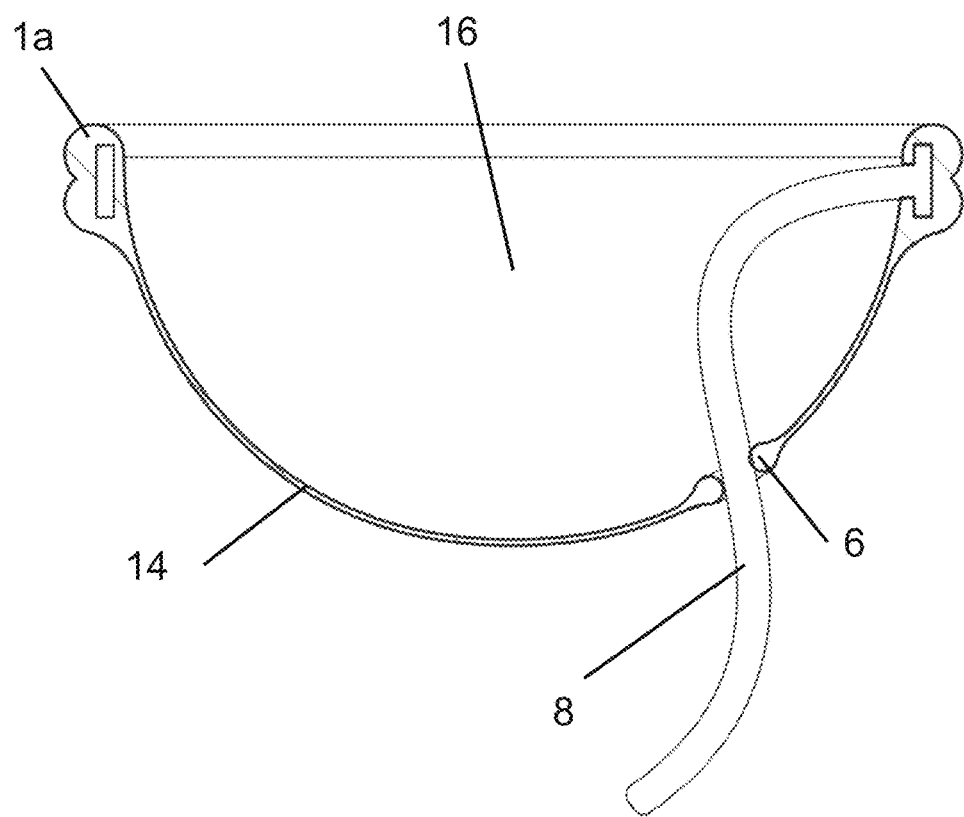
FIG. 6 illustrates a cross sectional view of a cup according to various embodiments.

Other embodiments of the cup 7 may include a cup 7 formed from an overmold process as illustrated in FIG. 6. In the overmold embodiment, the stem 8 may be composed of one part that is overmolded as a means to capture and affix the stem 8 to the cup 7. In accordance with many embodiments the overmolded design may be configured to operate in the same manner as any other embodiment described herein, where the stem 8 is pulled downward through the seal 6 thereby actuating the sidewall 14 of the cup 7.

Figure 7:
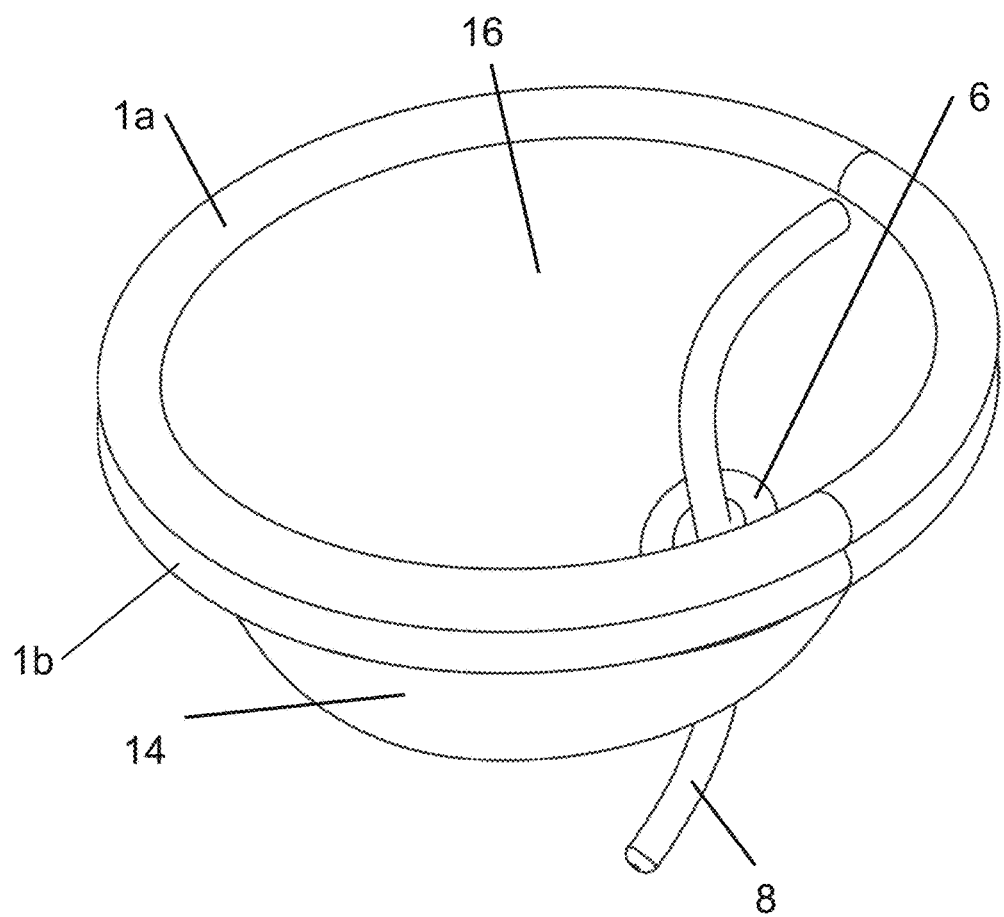
FIG. 7 illustrates a perspective view of a cup according to various embodiments.
Figure 8:
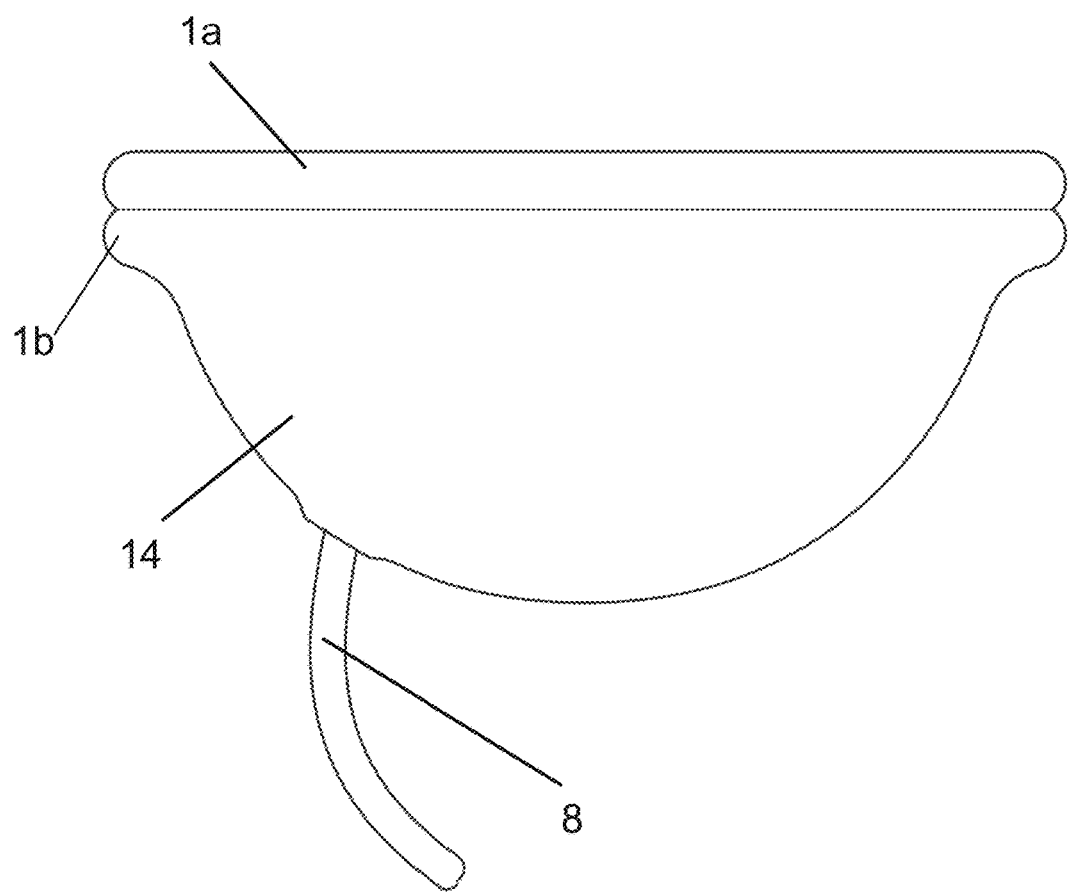
FIG. 8 illustrates a side view of a cup according to various embodiments.

In yet other embodiments the cup 7 is semicircular and the seal is located laterally on the cup as illustrated in FIGS. 6-8. For example, the cup as illustrated in FIGS. 6-8 may be configured such that the bottom portion 19 of the cup 7 has a bowl like shape having a semicircular cross section. In accordance with various overmold embodiments, the stem may extend from the lip 1 in the upper portion down through a portion of the sidewall in the lower portion of the cup 7 such that the seal 6 is located laterally to the central axis of the cup 7. Additionally, many embodiments may have a contoured rim 1a wherein the rim may have one or more contoured edges 1b as illustrated in FIGS. 7 and 8.

Figure 9:
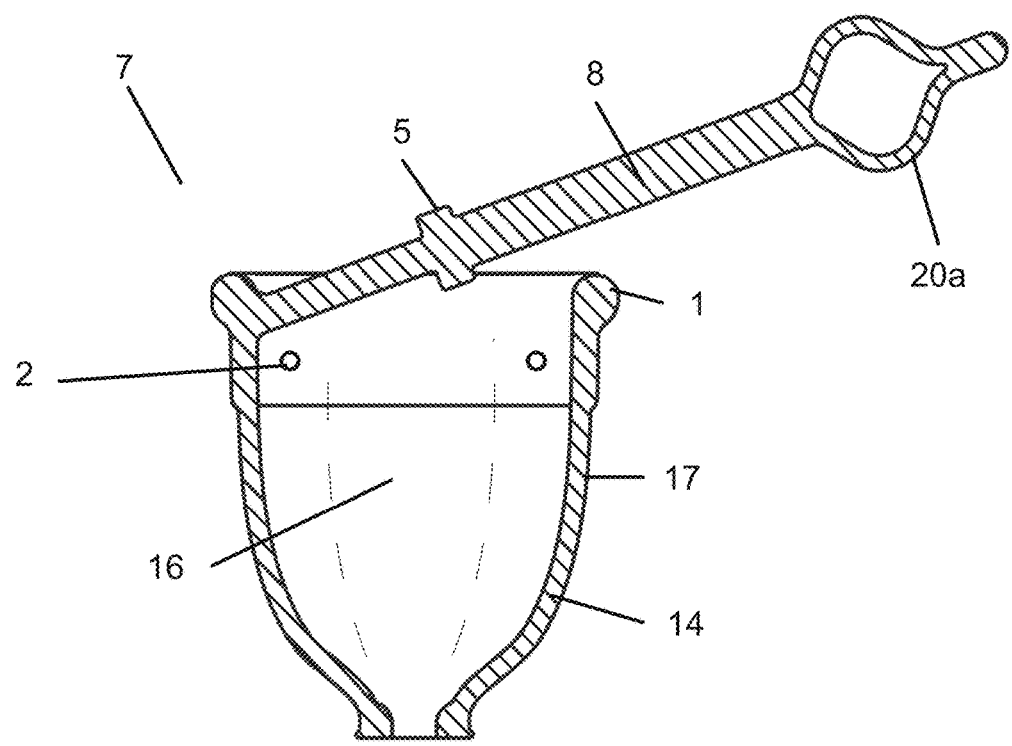
FIG. 9 illustrates an embodiment of the menstrual cup and stem with the stem removed from the cavity of the cup.

As is discussed throughout the specification the embodiments described herein are directed to a menstrual cup that is designed to better facilitate the insertion and removal process. As is described with respect to the stem, many embodiments of the cup 7 may incorporate an aperture 2 disposed within the sidewall 14 of the cup 7. FIG. 9 illustrates the stem 8 being removed from the seal according to various embodiments for clarity. As shown, in many embodiments the cavity portion 16 of the cup 7 has at least one aperture 2 disposed therein. The aperture 2 may be configured to run through the thickness of the sidewall and is configured in the same manner as the aperture 2 disposed within the stem 8. During use, the aperture 2 is closed off by the vaginal walls (not shown) when the cup is in a deployed shape allowing for a suction seal to be formed when in use. Pulling the stem 8 from below likewise would orient the aperture 2 vertically thereby creating a conduit for air between the region above and below the cup 7. The conduit of air would, in turn, allow for the release of the suction and facilitate the removal of the cup 7.

Actuation of the Cup Assembly

Figure 10:
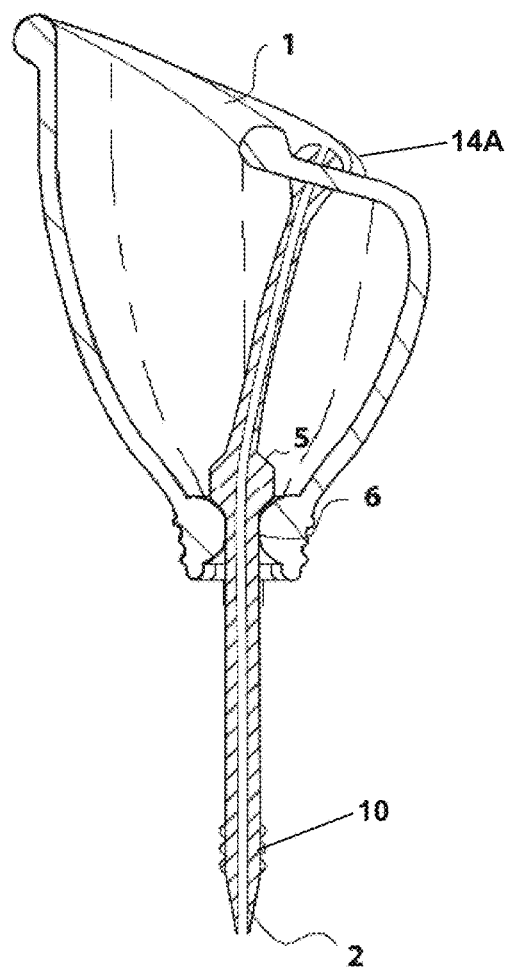
FIG. 10 illustrates an embodiment of the menstrual cup according to embodiments described herein.

Referring now to the embodiments directed to the actuation of the cup and stem to help facilitate the removal of the cup. FIG. 10 illustrates an embodiment of the actuation of the stem 8 through the seal 6 near the bottom portion of the cup 7. As shown, pulling the stem 8 through the seal 6 in a downward motion applies a proportionate force to the inner wall 15 of the sidewall 14 (as shown in FIG. 1) and creates a fold 14A in the sidewall of the cup. The folding of the sidewall 14 and rim 1 place the cup 7 in the folded configuration previously discussed. In the folded configuration the stem acts to pull the sidewall 14 and the rim 1 towards the center of the receptacle 13 such that the sidewall and rim are folded a predetermined distance.

As described earlier, the fold, in accordance with many embodiments aligns the aperture 2 such that the seal between the cup 7 and the vaginal walls (not shown) is released thereby facilitating the removal the cup by simply pulling downward on the stem. FIG. 10 illustrates the actuation of the cup according to various embodiments in which the aperture is disposed within the stem and the grasping means is a series of radial ridges 10.

Figure 11:
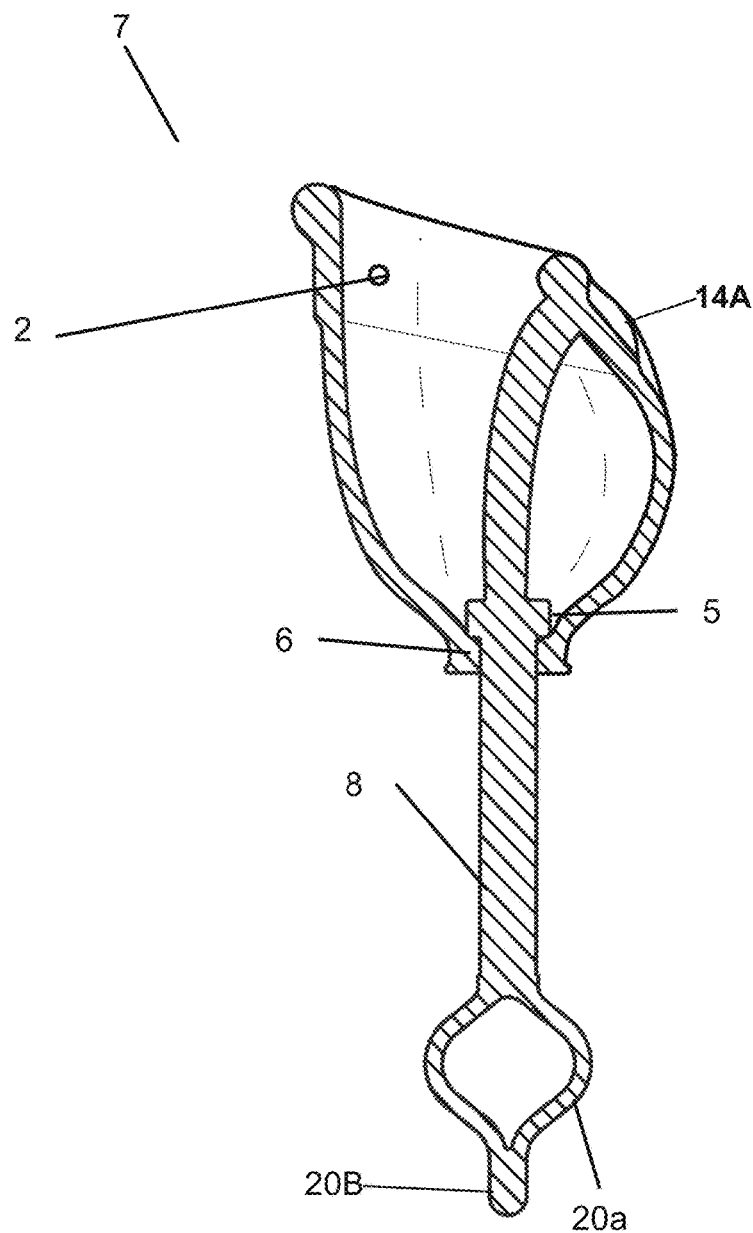
FIG. 11 illustrated an exemplary embodiment of the menstrual cup with an actuated stem.

FIG. 11 illustrates a similar actuation of the menstrual cup 7 according to embodiments comprising a stem with an opening 20A at the distal end 12. As shown, the opening, as previously described allows a user to pull downward with a single digit hooked through the opening 20A and thus actuate the sidewall 14 of the cup. As shown, such embodiments may have the apertures 2 disposed in the sidewall acting to relieve the seal formed from insertion and placing the cup 7 in a deployed state. When a typical menstrual cup is inserted properly it remains in place due to the natural suction that occurs from the interference with the cup and the vaginal walls. Embodiments described herein enable the user to more easily break that seal without extensive manual manipulation of the sidewalls of the cup. Although several embodiments are illustrated by the figures it should understood that the figures are not meant to be limiting and that any suitable configuration may be used.

Figure 12:
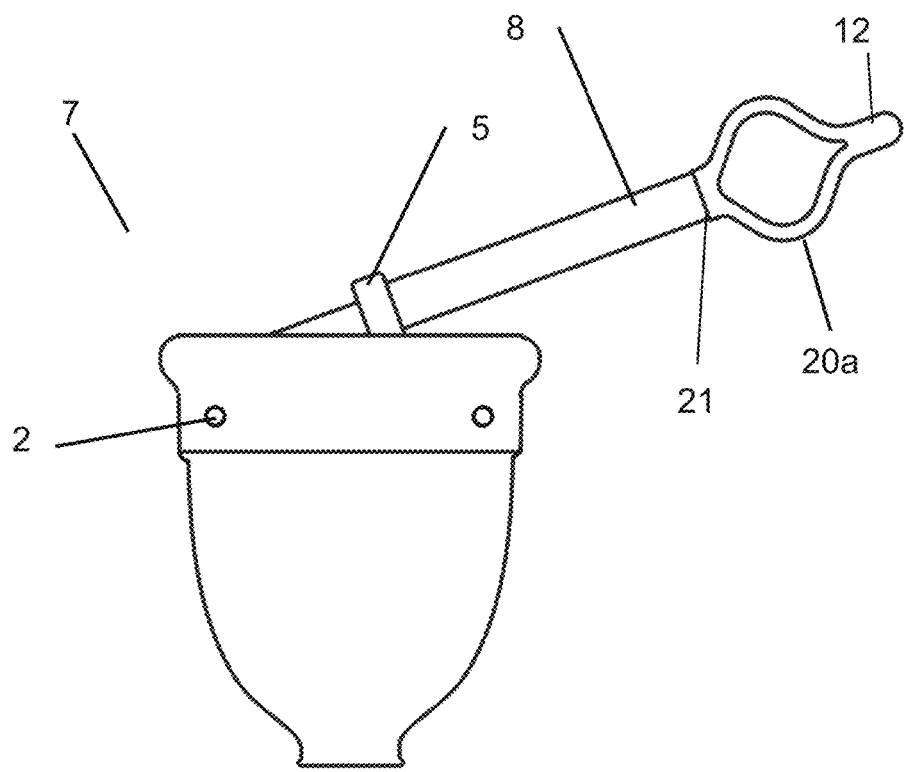
FIG. 12 illustrates a side view of an embodiment of the cup with a stem removed.

Turning now to FIGS. 12-14B various embodiments of the cup 7 and stem 8 actuations are shown. FIG. 12 for example shows the cup 7 according to embodiments in which the stem 8 has been removed from the cavity (not shown). As the use of the cup 7 may require periodic cleaning, the ability to remove the stem 8 from the cavity 16 of the cup may allow for easier cleaning of the various components as well as the seal 6 thereby making the use of the cup more hygienically appealing.

Figure 13A:
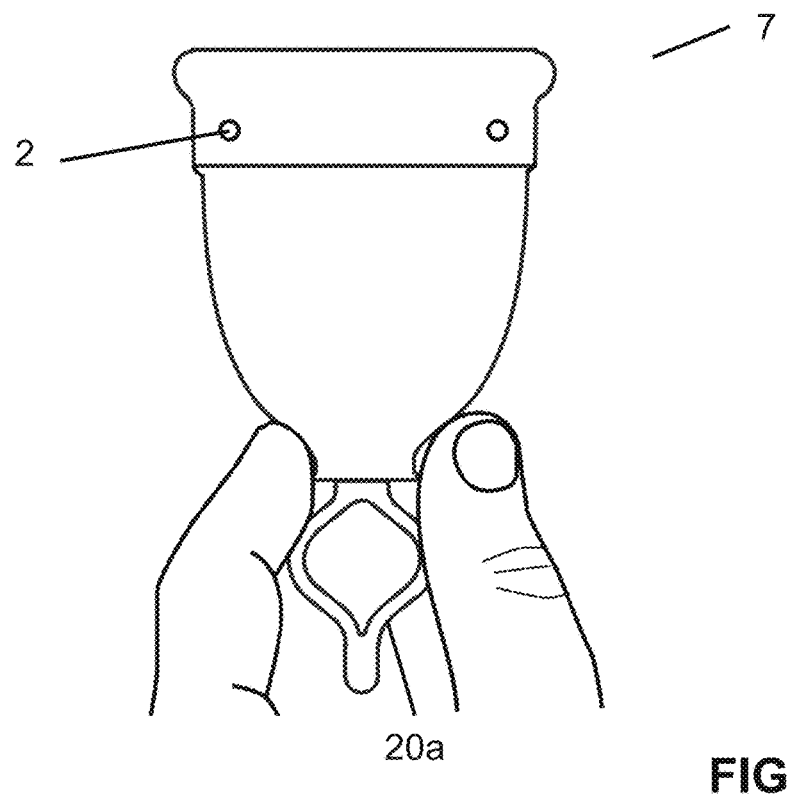
FIGS. 13A and 13B illustrate the actuation of the cup in accordance with various embodiments.

In accordance with many embodiments the stem 8 and the sidewall 14 of the cup 7 are designed to be actuated in a variety of ways. For example, FIG. 13A illustrates an embodiment in which the stem 8 may be grasped with a pinch like grasp. In many embodiments, the stem and cup are made from a resilient material such that the opening 20A may be compressed by a pinch like grasp as the user actuates the stem 8. Upon release of the stem 8 the opening 20A would remain in a deformed state due to friction in the interference seal 6 between the cup and the stem until a user resets the stem 8 by manually pulling on the stem 8 from the top side of the cup. A small ridge 21 (best illustrated in FIGS. 12 and 14B) on the stem 8 above the gripping region provides haptic feedback to users to indicate how far to pull when resetting the stem. Likewise, the sidewall may also resiliently deform when the stem 8 is actuated.

Figure 13B:
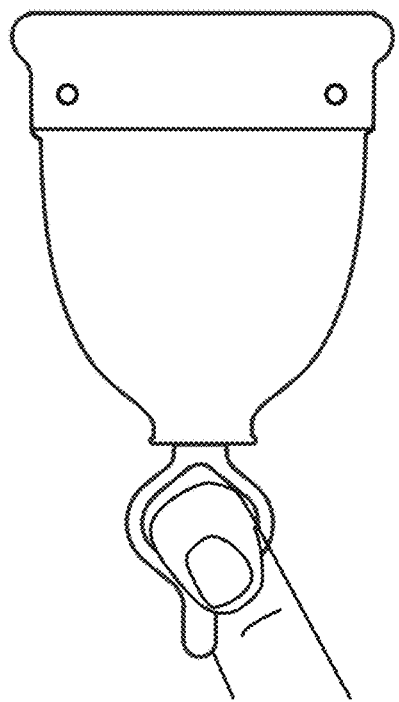

In other embodiments, the stem 8 may be actuated by the user by using a single digit in a hook like grasp. For example, FIG. 13B illustrates the users finger hooked through the opening 20A at the distal end 12 of the stem 8. The user then would pull in a downward motion and actuate the stem 8 and sidewall 14 of the cup 7. In accordance with many embodiments, as also previously described, the stem 8 may only be designed to move a predetermined distance due to the stop 5 positioned on the stem 8.

Figure 14A:
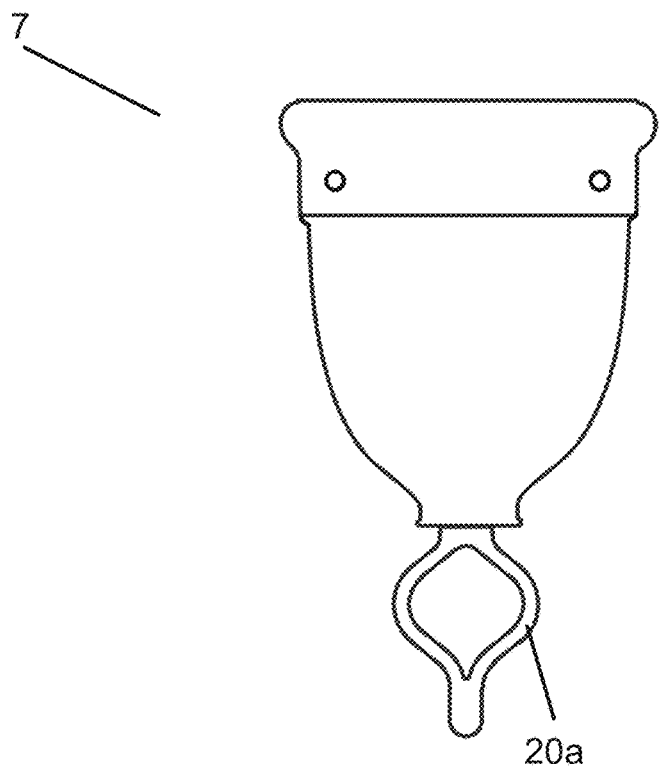
FIGS. 14A and 14B illustrate various positions of the stem accordance with many embodiments.
Figure 14B:
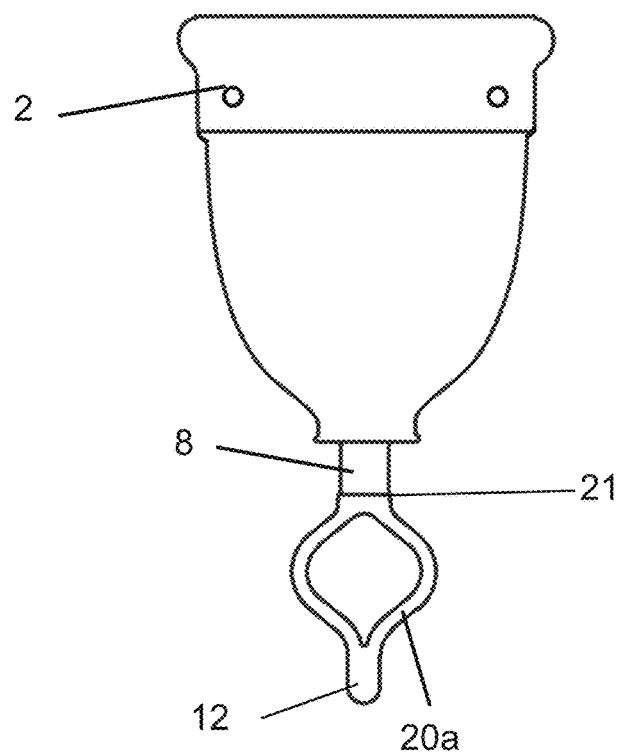

The motion of the stem 8 as discussed previously is best illustrated in FIGS. 14A and 14B. For example, in a deployed position, the stem 8 will be positioned up within the cavity as illustrated in FIG. 14A such that the opening 20A is positioned near the bottom portion 19 of the cup 7. Additionally, when actuated the stem 8 is positioned such that the opening is located distally from the bottom portion 19 of the cup, as illustrated in FIG. 14B. The stem 8 passing through the seal 6 provides for adjustable stem length that can accommodate a larger range of user anatomy including longer vaginal canals. The stem 8 resides in cavity of the cup 7 and can include extra length of material such that the stem 8 gripping region 20A may be positioned in a proximal state FIG. 10A and positioned in a distal state FIG. 10B and any state in between without actuating the sidewall. Further deflection of the stem begins to actuate the sidewall.

Figure 15:
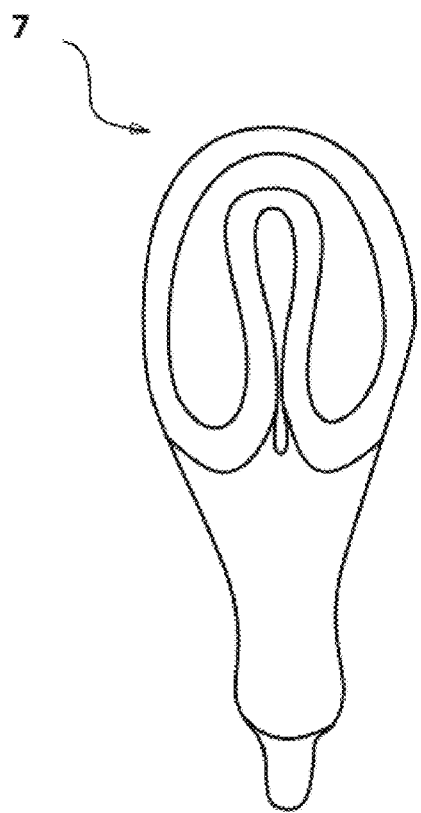
FIG. 15 illustrates a manner of folding for inserting the menstrual cup in accordance with known practices.

According to many techniques known in the art, one method of folding for insertion is illustrated in FIG. 15.

Figure 16:
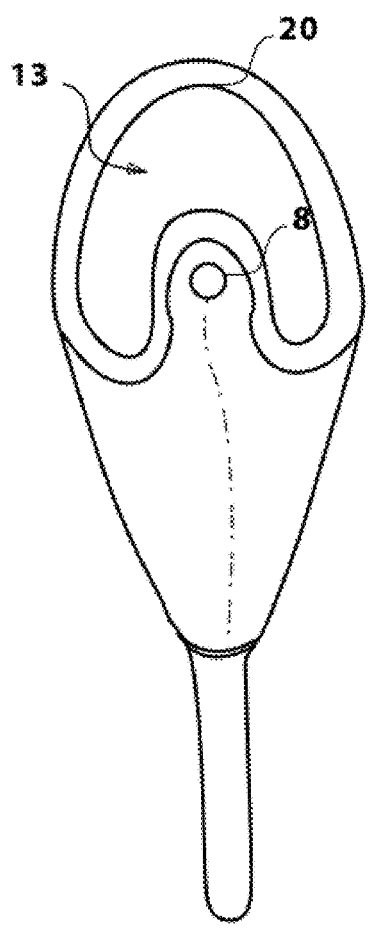
FIG. 16 Illustrates an exemplary embodiment of the invention during removal.

In accordance with many embodiments, the cup 7 may be partially folded for removal as well as insertion. The partial folding for removal, in accordance with various embodiments, and described previously is illustrated further in FIG. 16. As shown, menstrual cups in accordance with current embodiments allow for the removal of the cup with a predetermined deformed configuration. In particular, the presence of the stop 5 on the stem 8 allows for the receptacle 13 volume to remain large thus minimizing the risk of fluid spill during removal.

In accordance with many embodiments, after insertion the natural spring force of the cup 7 may provide enough force to restore the stem 8 to a nominal position as well as open the cup to its natural relaxed state. In many preferred embodiments, the cup 7 may be formed of any type of resilient material that is impervious to liquid. In some embodiments the cup 7 may be formed of medical grade silicone. In some embodiments the cup 7 and stem 8 are the same material. In some embodiments the cup 7 and stem 8 are different materials. In some embodiments the stem 8 is made of a string. In accordance with some embodiments the cup 7 may be coated in a moisture barrier such as parylene.

Embodiments of the Applicator

Various embodiments also provide a system for removal and insertion of the cup with an applicator 170, as shown in FIG. 17 through FIG. 21. In many such embodiments, the applicator may comprise three primary components depicted in an exploded view in FIG. 17, which include a main body 22, an actuator 29, and paddles 32 for insertion.

Figure 17:
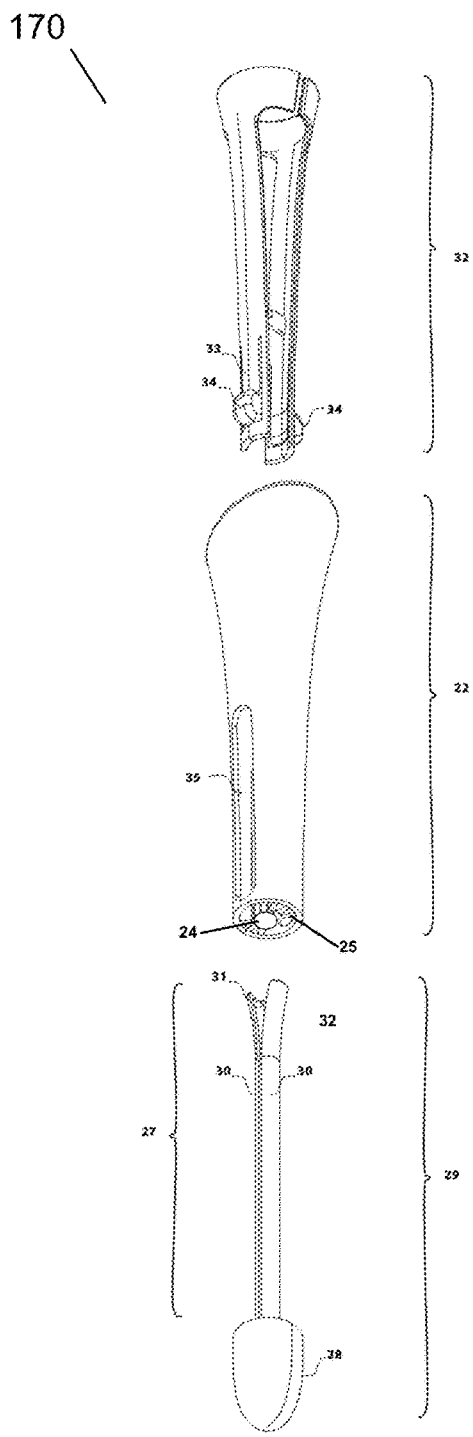
FIG. 17 illustrates an embodiment encompassing the insertion of the menstrual cup in accordance with various embodiments described herein.
Figure 18:
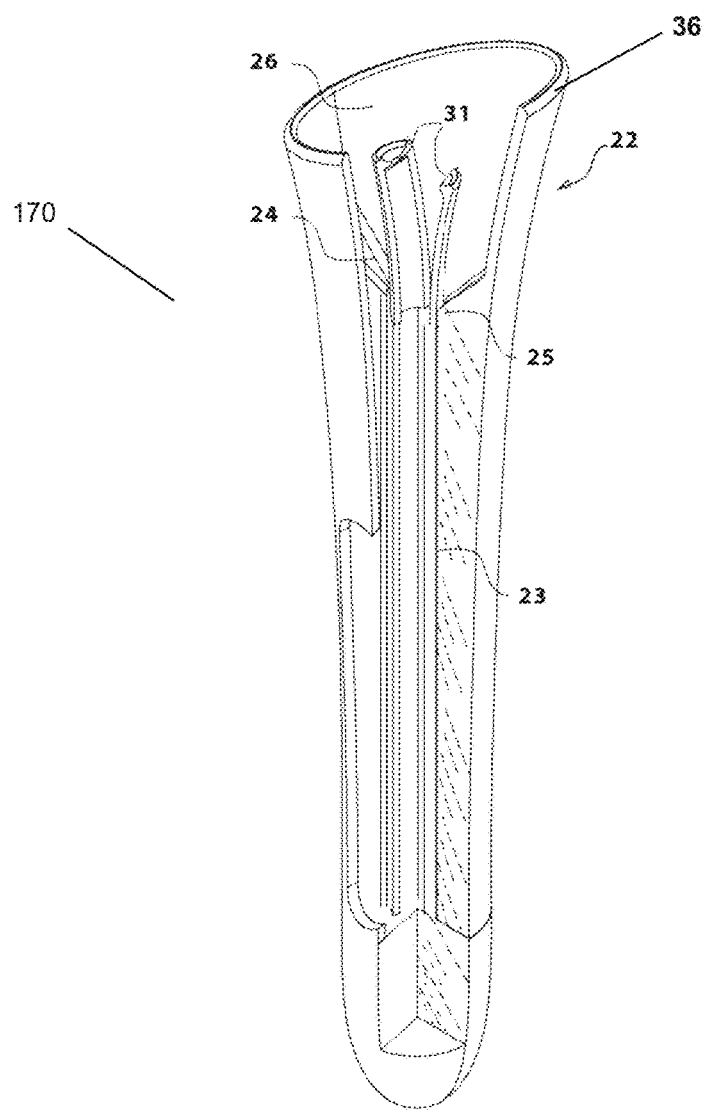
FIG. 18 illustrates an insertion device in accordance with various embodiments.

Now referring to FIGS. 17 and 18, the applicator body 22 may be conical in shape and further comprise a receiving cavity 23 with inner contours 26 that correspond in shape with the cup outer wall surface 17. According to many embodiments, the receiving cavity 23 may be slanted creating a leading edge 36 that when advanced in a helical fashion into the vagina (not shown) serves to concentrically center the cup 7 with respect to the applicator. The body of the applicator 22 may further comprise an internal cylindrical shaft 24 formed from ribs 25 which create a constriction area at the terminus of the cylindrical shaft 24 just below the receiving cavity 23.

As shown in FIGS. 17 and 18, in many embodiments, the actuator 29 may comprise a gripping mechanism 27 and a handle 28. The gripping mechanism 27 may be comprised of two curved beams 30 that plastically deform into a cylindrical cross-section (shown in FIG. 19) when pulled back through the constriction area formed by the ribs 25 of the body 22.

In accordance with many embodiments, the distal end of the beams 30 comprise teeth 31 which form an inner diameter that is less than the outer diameter of the stem 8 when the beams straighten. The teeth 31 may be designed to clamp around the stem 8 of the cup 7 to hold the cup in position during insertion and removal. In accordance with many embodiments the teeth may be a continuous structure attached to the beams. Although certain embodiments are illustrated it should be understood that any number of configurations may be used.

Figure 19:
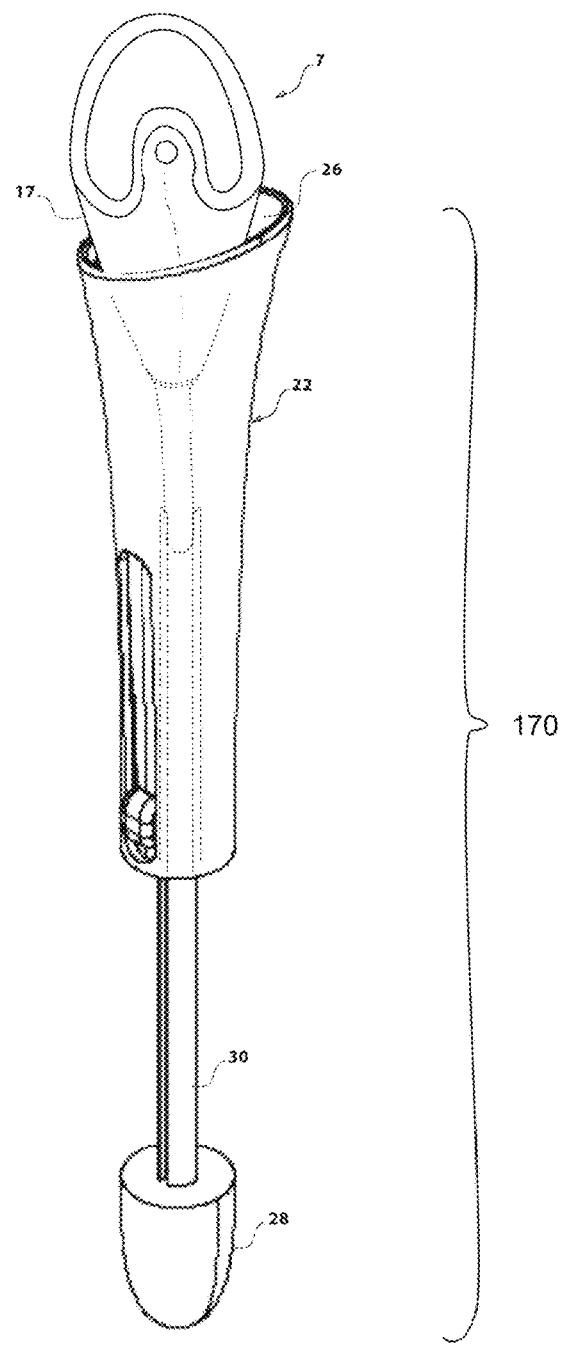
FIG. 19 illustrates the insertion device in accordance with various embodiments described herein.
Figure 20:
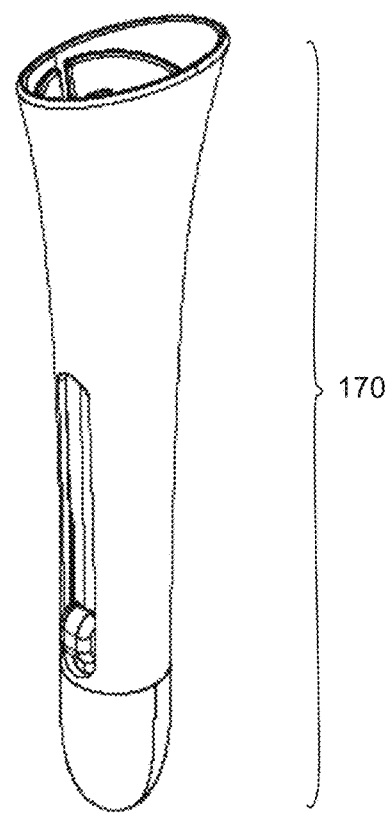
FIG. 20 illustrates an exploded view of an insertion device in accordance with various embodiments described herein.

Referring back to FIG. 17, the paddles 32, according to many embodiments may be designed to fit within the applicator body 22 and surround the actuator 29. Additionally, many embodiments utilize the paddles 32 to ensure the proper insertion and removal of the cup 7. In accordance with many embodiments, the paddles 32, may have snaps 33 that interface with grooves 35 on the applicator body 22. The snaps 33 may be configured with protruding bodies 34 that will allow for a user to manually slide the paddles 32 into a deployed position shown in FIG. 21, for insertion and/or into a retracted position for removal of the cup, as shown in FIG. 19. In accordance with many embodiments the protruding bodies 34 may be ergonomically designed for improved functionality in users. Furthermore, many embodiments of the paddles 32 may contain sections of removed material to allow for greater flexibility and/or weight savings.

In accordance with many embodiments, the applicator 170 may be configured to remove the cup 7 as shown in FIG. 19. To remove the cup 7, the applicator 170 is first inserted into the vagina (not shown) and advanced helically, whereby the leading edge 36 of the body 22 applies a screwing force on the cup stem 8 and outer wall surface 17 that concentrically centers the cup 7 with respect to the applicator 170. Once the applicator is advanced so that the cup 7 is resting in the applicator receiving cavity 23, the user may pull on the handle 28 of the actuator 29 causing the beams 30 and teeth 31 to clamp onto and pull down on the cup stem 8 thereby actuating and folding the cup rim 1 and sidewall 14 into a position optimized for removal and pouring of menses. The applicator 170 may then be removed from the vagina (not shown) and the menses may then be poured out.

Figure 21:
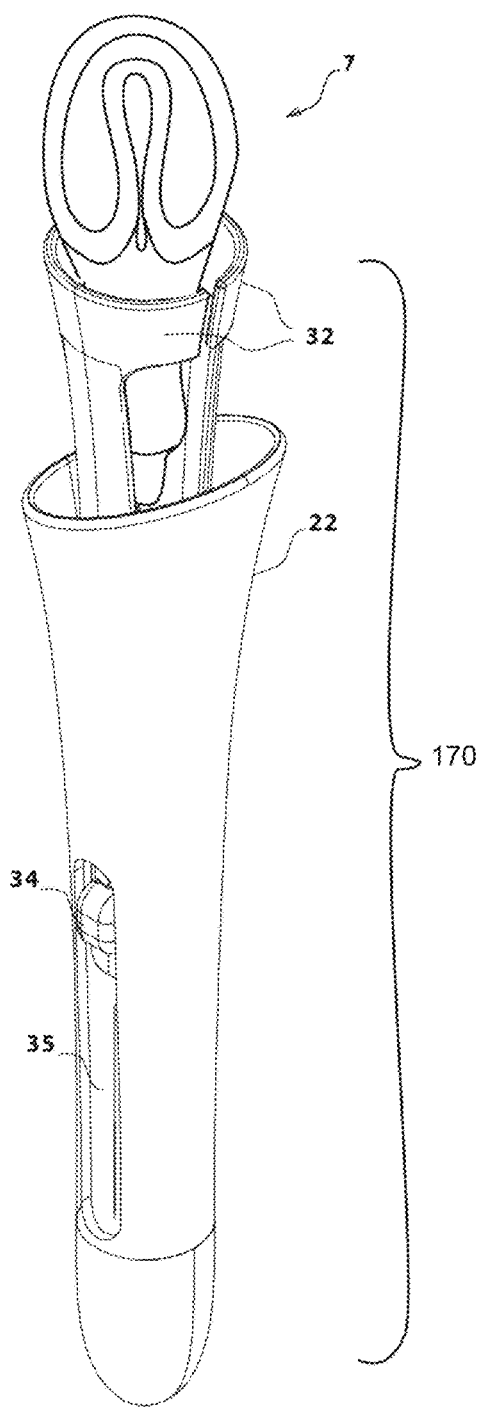
FIG. 21 is a cross sectional view of an insertion device in accordance with many embodiments described herein.

In accordance with other embodiments, the applicator 170 may be configured for inserting the cup 7, as illustrated in FIG. 21. To insert the cup 7, the user may slide the paddles 32 by pushing on the protruding bodies 34 thereby deploying the paddles 32 (shown in FIG. 21). The cup 7 is folded in half and inserted into the paddles 32. The outer diameter of the paddles 32 corresponds to the folded diameter of the cup 7. The applicator 21 and cup 7 are then inserted into the vagina (not shown). Once the cup 7 is in a desired location, the user pulls down on the protruding bodies 34 and thus slide the paddles 32 down allowing the cup 7 to expand under its own spring force into a deployed shape (not shown). It is noted that with the use of an applicator, the cup may be inserted further inside the vagina (not shown) where the tissue is less sensitive than can be achieved with digital insertion.

In accordance with some embodiments the insertion and removal of a menstrual cup by way of the applicator described herein may be assisted by a resilient device. In many embodiments the resilient device may be a spring disposed within the applicator and configured to aid in the engagement between the body 22, the paddles 32 and the actuator 29.

Referring now to FIGS. 22-28 a process of manufacturing the menstrual cup described herein is described according to many embodiments. Given the nature and complexity of a menstrual cup with an integrated stem system for actuating the sidewall, the design and manufacture of such a product may be more complex than the traditional molding process. As previously described, according to many embodiments the menstrual cup described herein may be manufactured of a resilient material such as for example, a medical grade silicone material.

The traditional process of manufacture of a menstrual cup made of a resilient material will involve designing the cup in the desired configuration. Typical menstrual cup designs have a cup portion and a lower stem portion affixed to the bottom portion of the cup. The traditional method for manufacturing previous designs uses injection molding. The molding tooling typically consists of several parts that once removed the end product or menstrual cup is left. Only minor trimming may be required to remove excess material from around the product. Such traditional processes would be too time consuming and too costly to adequately produce the novel design described herein. As such a new method for manufacturing would be needed.

Figure 22:
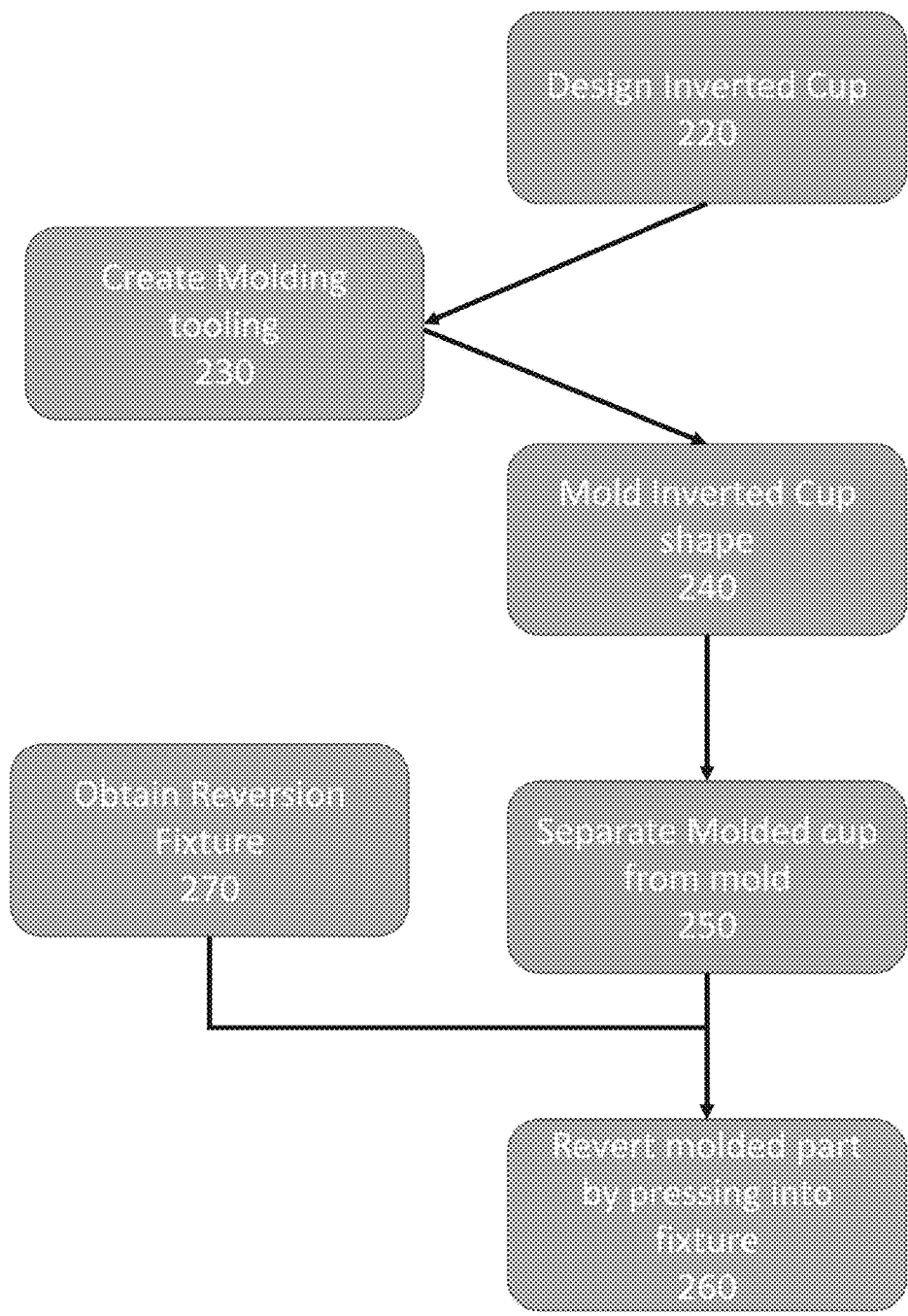
FIG. 22 illustrates a process flow of the manufacture of a cup according to various embodiments.

In accordance with many embodiments described herein, the manufacturing process may be described according to FIG. 22. FIG. 22 illustrates the process by which an inverted mold design is first created 220. Once the inverted design is created 220 the mold tooling can be manufactured 230 accordingly to allow for molding the cup. The manufacturing tooling, according to various embodiments will be described further herein. Once the tooling is in place the inverted part may be molded 240. During the molding process or prior to, a reversion tooling fixture may be obtained 270 to aid in producing the final product. Once the molding process is complete the inverted molded cup may be removed from the tooling 250. Once removed from the tooling the product must be reverted back to its final usage state by inverting the inverted part. This can be done by a variety of reversion processes 260 described herein.

The Inverted Design

Figure 23:
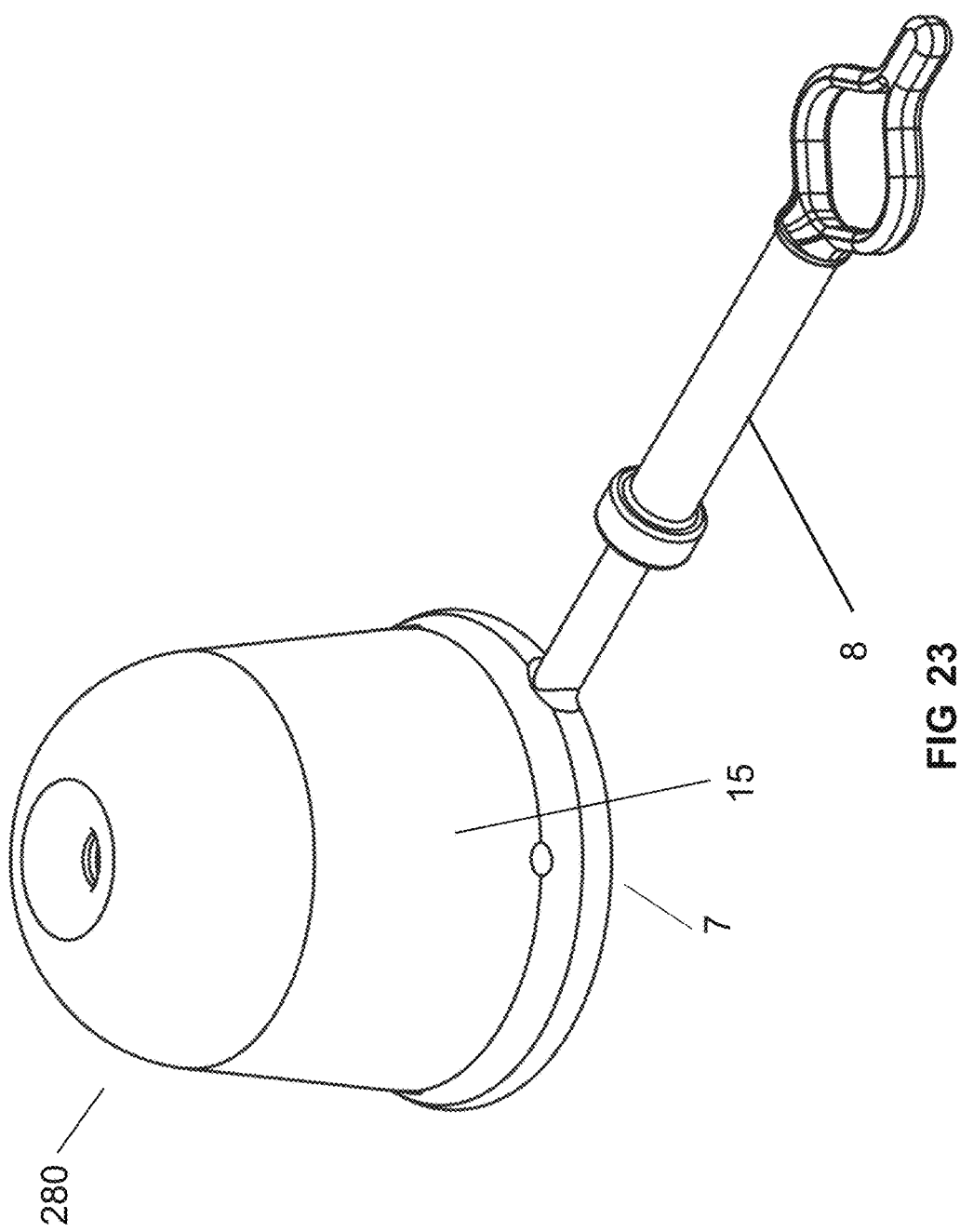
FIG. 23 illustrates a perspective view of a molded cup inverted design according to many embodiments.

According to many embodiments the design of the menstrual cup with a stem that actuates the sidewall for ease of removal would be better facilitated by designing the cup to be molded in the inverted shape. FIG. 23 illustrates an inverted molded cup design 280 with the cup 7 and stem 8 according to many embodiments. What is illustrated in FIG. 23 is the inner wall 15 being exposed while the outer wall 17 is in contact with a bottom half of the mold tooling. In other words FIG. 23 illustrates an inverted shape as compared to FIG. 1 of the menstrual cup.

Figure 24:
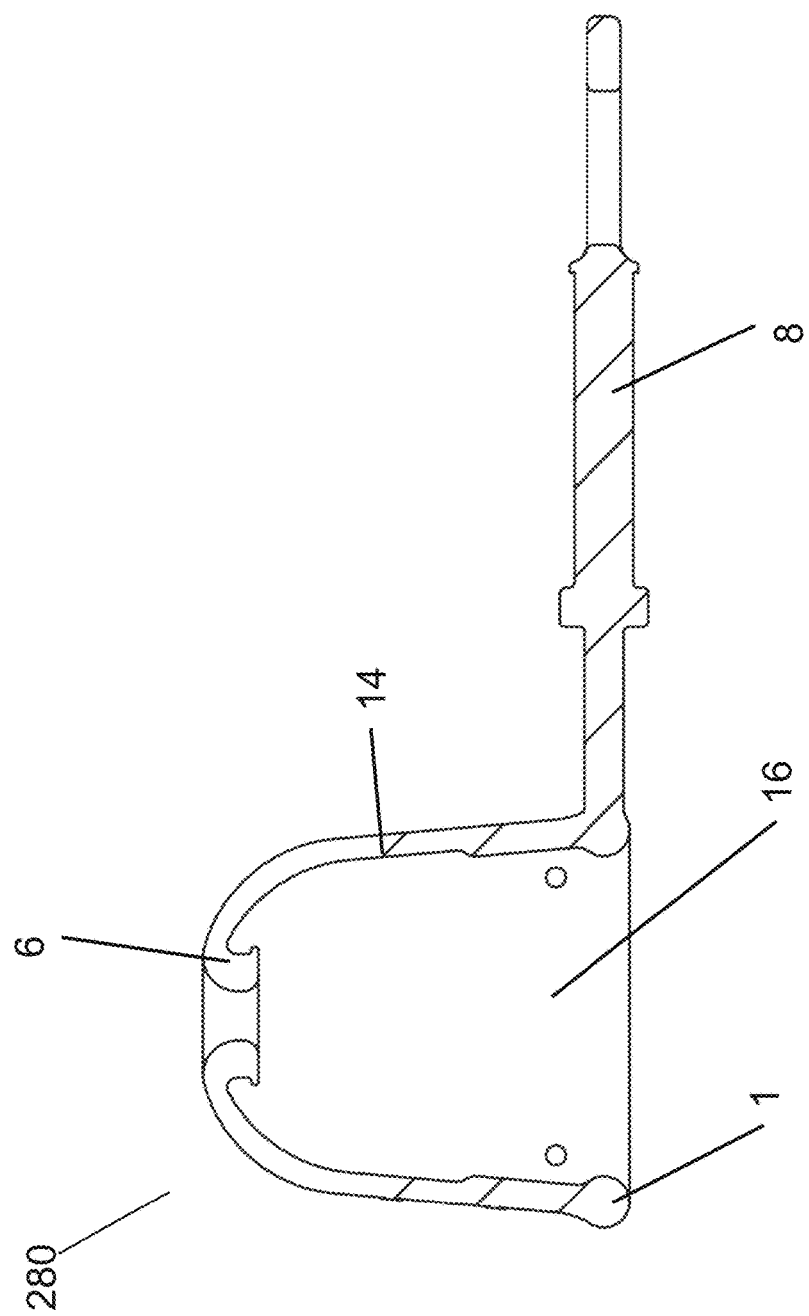
FIG. 24 illustrates a cross sectional view of an inverted design of a cup according to many embodiments.

Referring to FIG. 24, a cross sectional view of the inverted cup design 280. It can be seen in FIG. 24 that the same components as illustrated in FIG. 1 are illustrated in FIG. 24 with an inverted design. The inversion is seen by the lower portion 19 as described earlier now appears to be the upper portion of the design for the purpose of manufacturing. The inverted design as illustrated in FIGS. 23 and 24 improved on the traditional methods because it simplifies the tooling and overall process of molding the cup and extracting the part. To mold the cup in an "as used" configuration as illustrated in FIG. 1 would require far more complex tooling with a variety of components to achieve the desired shape and size of the menstrual cup. By inverting the design, the tooling can be simplified to two components.

Mold Tooling

Figure 25:
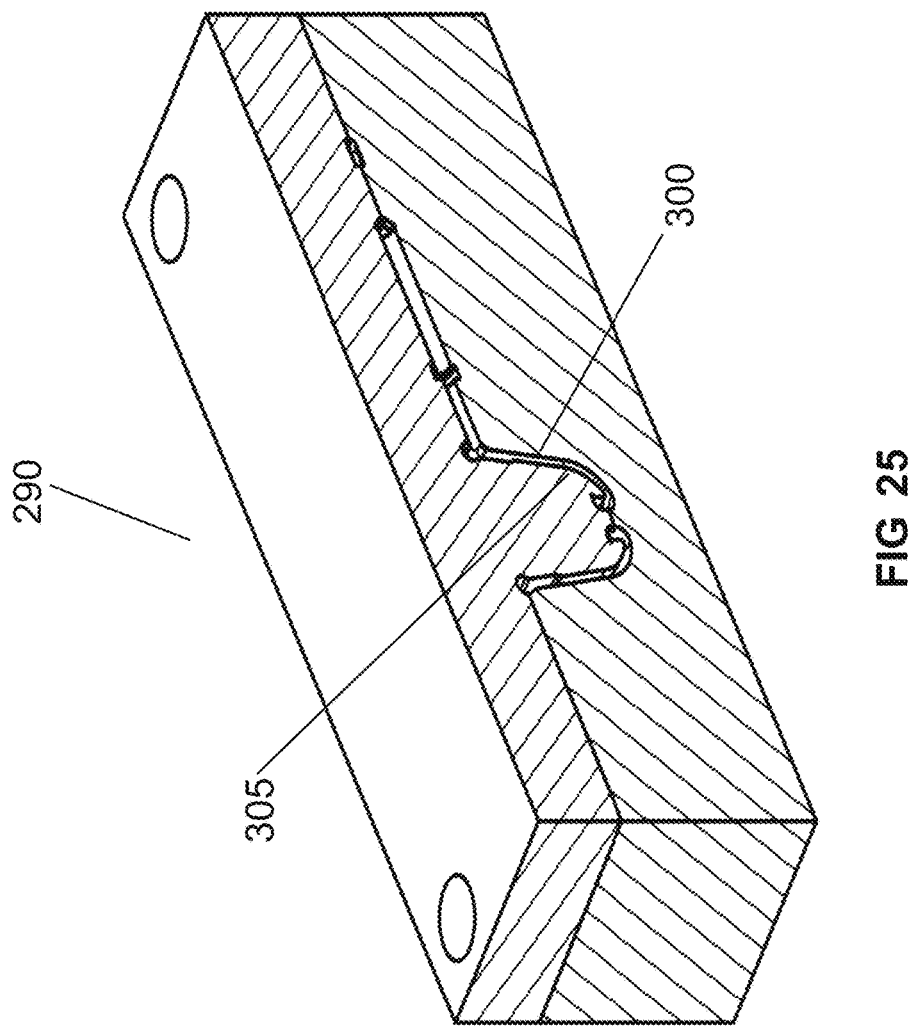
FIG. 25 illustrates a cross sectional view of an inverted design mold tooling set according to various embodiments.
Figure 26:
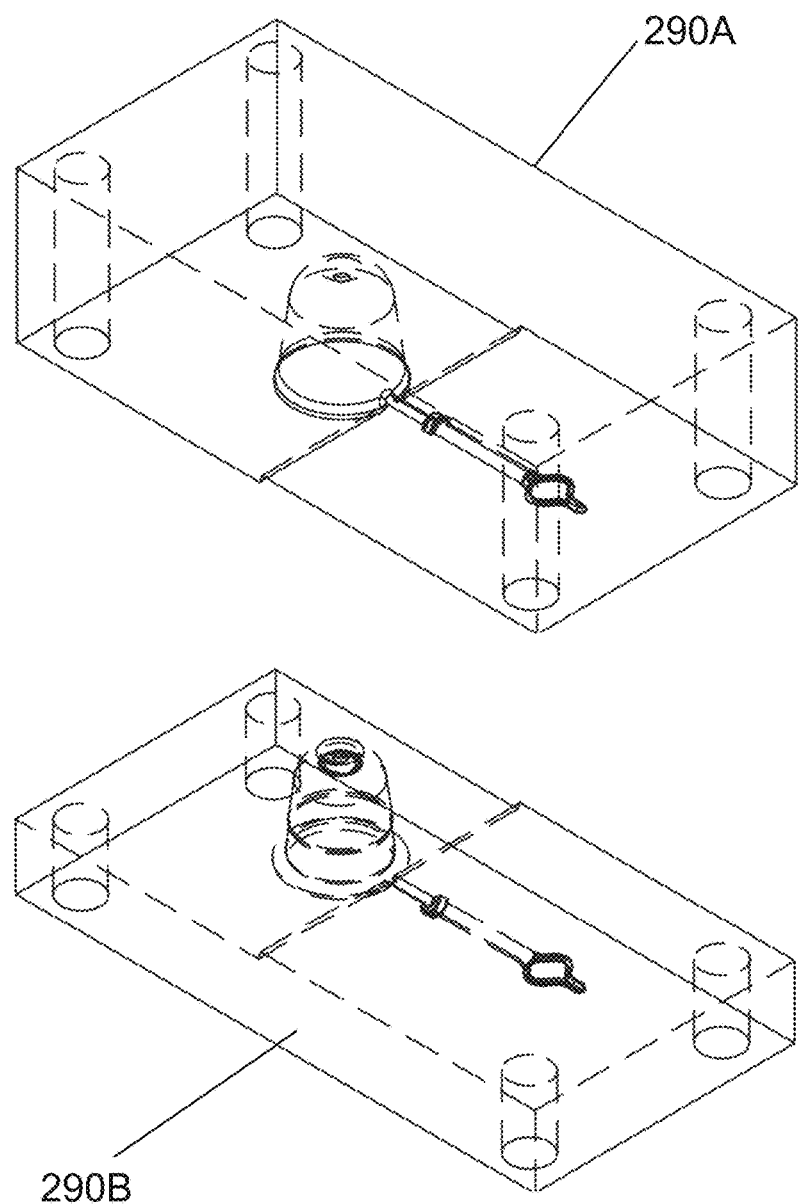
FIG. 26 illustrates a perspective view of inverted design molding tooling according to various embodiments.

Turning now to FIGS. 25 and 26 the inverted mold tooling is illustrated according to various embodiments. FIG. 25 illustrates a cross sectional view of an inverted mold tooling design according to various embodiments. The inverted mold tooling 290 may comprise multiple components as illustrated in FIG. 26. A top component 290A and a bottom component 290B. The top component 290A may contain the portion of the mold that would correspond to the internal surface of the cup indicated by 300 in FIG. 25. The bottom component 290B may correspond to the external surface of cup indicated by 305 in FIG. 25. The two components may be joined and the inverted part 280 may be molded using any number of processes. In accordance with many embodiments the molding process may be done by injection molding or over molding.

Extraction and Reversion

Figure 27:
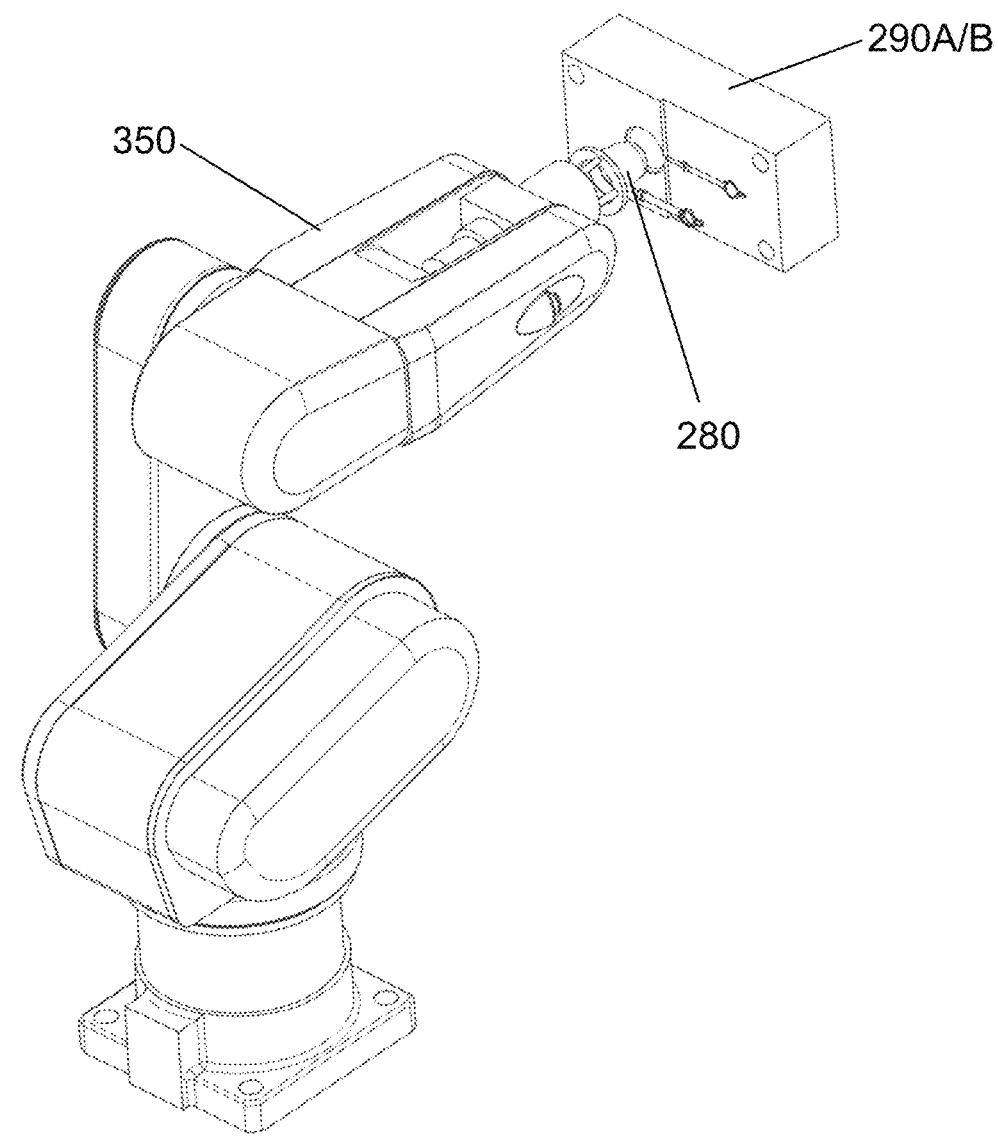
FIG. 27 illustrates a process of removing the inverted molded cup from the tooling according to various embodiments.
Figure 28:
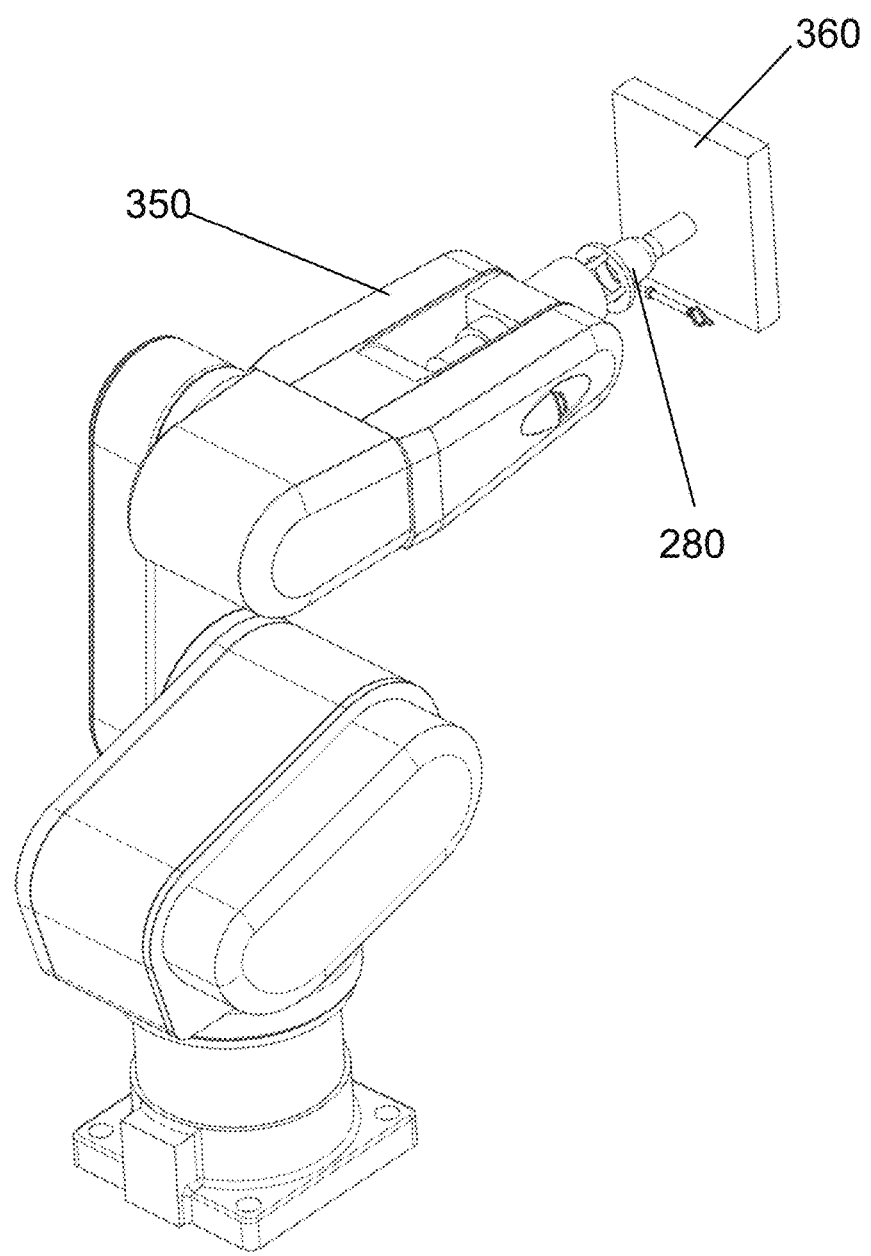
FIG. 28 illustrates a process of reverting the inverted molded cup according to various embodiments.

Turning now to FIGS. 27 and 28 the removal or extraction process, according to various embodiments is described. FIG. 27 illustrates an embodiment in which a portion of the molding tooling has been removed and the inverted molded part 280 remains in a portion of the tooling. According to various embodiments a robotic arm 350 may then be used to remove the inverted molded part 280 from the tooling. The robotic arm 350 illustrates a simple method of removal that may allow for simplified handling and improved processing time since the robotic arm 350 may be configured with any number of necessary tooling to help extract the part 280 from the tooling. Although a robotic arm is illustrated it should be understood that any number of methods for extraction may be used.

Once the inverted molded part 280 has been removed from the tooling it must be reverted to the desired final product shape. According to many embodiments illustrated herein, a reversion tool 360 may be designed and used to revert the inverted molded shape 280 to the desired end product. The reversion tooling 360 may take on any number of forms, for example it may be a simple plate with a stem portion extending outward from the plate. The stem portion may be configured to engage the lower portion of the cup in its inverted shape and depress the lower portion until the cup takes on the desired end product shape. According to various embodiments the stem may be configured to be similar to a portion of the mold tooling. In other embodiments the reversion tooling may be a portion of the mold tooling. According to various embodiments, a robotic arm 350 may be used to handle the inverted part 280 during the reversion process.

DOCTRINE OF EQUIVALENTS

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A menstrual cup comprising:
   a receptacle having a resiliently foldable rim defining a generally circular perimeter in an unfolded state, a sidewall having an inner wall surface defining a cavity therein, the cavity having a top portion proximal to the foldable rim with a first opening and a bottom portion with a second opening, wherein the cavity is configured to collect a fluid; and
   an elongated stem having a proximal end and a distal end and an elongated middle portion therebetween wherein the proximal end is attached to the sidewall,
   wherein the stem seats within the second opening to form a fluid seal therewith;
   wherein the manipulation of the distal end of the elongated stem applies a pulling force to the inner wall surface whereby a fold in the sidewall is created; and
   wherein the receptacle may have at least two positions:
      a folded position wherein the fold in the sidewall extends inward towards the center of the cavity; and
      a deployed position wherein the foldable rim is unfolded such that the first opening of the top portion conforms to the generally circular perimeter of the unfolded resiliently foldable rim.

2. The menstrual cup of claim 1, wherein the bottom portion of the cup is further configured to form an interference fit with the stem.

3. The menstrual cup of claim 1, wherein the stem further comprises a stop disposed at a point along the length of the stem.

4. The menstrual cup of claim 1, wherein the cup is formed of a material selected from a group consisting of silicone material and a thermoplastic elastomer.

5. The menstrual cup of claim 2, wherein the seal is configured to be reinforced material such that it is thicker than the sidewall.

6. The menstrual cup of claim 2, wherein the seal is selected from a group consisting of a radial seal and a wiper seal.

7. The menstrual cup of claim 1, wherein the stem comprises a resiliently foldable ring configured to cooperatively engage with a groove formed into the foldable rim and the side wall of the receptacle such that the depth of groove does not exceed the thickness of the sidewall, and wherein the ring is configured to pull against the foldable rim, sidewall, and inner wall when the stem is actuated and pulled by the user.

8. The menstrual cup of claim 1, wherein the stem is a continuous extension of the foldable rim.

9. The menstrual cup of claim 1, wherein the stem further comprises an elongated aperture configured to extend from the proximal end through the distal end whereby air pressure may be appropriately balanced in each of the folded and deployed positions.

10. The menstrual cup of claim 1, further comprising at least one hole to equalize the pressure for the removal of the cup.

11. The menstrual cup of claim 10, wherein at least one hole is disposed through the elongated stem.

12. The menstrual cup of claim 10, wherein the at least one hole is disposed through the sidewall of the cup near the top portion.

13. The menstrual cup of claim 1, wherein the distal portion of the stem further comprises grip enhancements.

14. The menstrual cup of claim 13, wherein the grip enhancements are selected from a group consisting of ridges, spiral ridges, a loop, a ring, and independent structures.

15. The menstrual cup of claim 1, wherein the cup is coated in parylene.

16. The Menstrual cup of claim 1, wherein the proximal end of the elongated stem is connected to the inner wall of the receptacle and the elongated middle portion is configured to pass through the cavity and the second opening of the bottom portion of the receptacle such that the distal end extends below the receptacle.

17. A method of manufacture of a menstrual cup comprising: Designing an inverted menstrual cup having a receptacle having a resiliently foldable rim defining a generally circular perimeter in an unfolded state, a sidewall having an inner wall surface defining a cavity therein, the cavity having a top portion proximal to the foldable rim with a first opening and a bottom portion with a second opening, wherein the cavity is configured to collect a fluid; and an elongated stem having a proximal end and a distal end and an elongated middle portion therebetween wherein the proximal end is attached to the sidewall, wherein the stem seats within the second opening to form a fluid seal therewith;

wherein the manipulation of the distal end of the elongated stem applies a pulling force to the inner wall surface whereby a fold in the sidewall is created; and wherein the receptacle may have at least two positions:

a folded position wherein the fold in the sidewall extends inward towards the center of the cavity; and a deployed position wherein the foldable rim is unfolded such that the first opening of the top portion conforms to the generally circular perimeter of the unfolded resiliently foldable rim;

Obtaining mold tooling configured to align with the inverted menstrual cup design;

Molding the inverted menstrual cup with the mold tooling;

Extracting the inverted menstrual cup from the molding;

Reverting the menstrual cup to a desired final shape.

18. The menstrual cup of claim 7 wherein the ring is overmolded into the cup.

19. The menstrual cup of claim 1 wherein the stem is a string wherein the string is molded into the cup.

20. The menstrual cup of claim 19 wherein the string is molded into the cup by a method selected from a group consisting of co-molding and overmolding.

* * * * *